United States Patent
Goldfarb et al.

(10) Patent No.: US 12,324,913 B2
(45) Date of Patent: Jun. 10, 2025

(54) METHOD AND DEVICE FOR TREATING MICROSCOPIC RESIDUAL TUMORS REMAINING IN TISSUES FOLLOWING SURGICAL RESECTION

(71) Applicant: Grand Decade Developments Limited, Hong Kong (HK)

(72) Inventors: Paul Goldfarb, San Diego, CA (US); Dietmar Rabussay, Solana Beach, CA (US)

(73) Assignee: Grand Decade Developments Limited, Hong Kong (HK)

( * ) Notice: Subject to any disclaimer, the term of this patent is extended or adjusted under 35 U.S.C. 154(b) by 1087 days.

(21) Appl. No.: 17/235,649

(22) Filed: Apr. 20, 2021

(65) Prior Publication Data

US 2021/0308451 A1 Oct. 7, 2021

Related U.S. Application Data

(60) Continuation of application No. 15/488,288, filed on Apr. 14, 2017, now Pat. No. 11,007,365, which is a
(Continued)

(51) Int. Cl.
*A61N 1/32* (2006.01)
*A61K 9/00* (2006.01)
(Continued)

(52) U.S. Cl.
CPC ............ *A61N 1/327* (2013.01); *A61K 9/0009* (2013.01); *A61K 38/14* (2013.01); *A61M 5/19* (2013.01); *A61M 5/20* (2013.01)

(58) Field of Classification Search
CPC ........ A61N 1/327; A61N 1/30; A61K 9/0009; A61K 38/14; A61M 5/19; A61M 5/20; A61P 35/00; A61P 43/00
See application file for complete search history.

(56) References Cited

U.S. PATENT DOCUMENTS

| | | | |
|---|---|---|---|
| 5,993,434 | A | 11/1999 | Dev et al. |
| 6,014,584 | A | 1/2000 | Hofmann et al. |

(Continued)

FOREIGN PATENT DOCUMENTS

| | | |
|---|---|---|
| EP | 1142606 A2 | 10/2001 |
| JP | 2000-503586 A | 3/2000 |

(Continued)

OTHER PUBLICATIONS

Burian et al., "Electroporation therapy in head and neck cancer", Acta Otolaryngol (2003) 123:264-268.
(Continued)

*Primary Examiner* — Chelsea E Stinson
*Assistant Examiner* — Nelson Louis Alvarado, Jr.
(74) *Attorney, Agent, or Firm* — Wolf, Greenfield & Sacks, P.C.

(57) ABSTRACT

This invention concerns treating apparently normal tissue surrounding sites of cancerous tumors so as to reduce both the probability of a recurrence of cancer at and near the site of a cancerous tissue, and to reduce the amount of apparently healthy tissue that is usually excised along with the tumor, thereby providing a substantial benefit to the cancer patient by eliminating or delaying tumor recurrence and sparing normal tissue for its functionality and for avoiding unnecessary disfigurement.

14 Claims, 18 Drawing Sheets

Related U.S. Application Data continuation of application No. 13/278,721, filed on Oct. 21, 2011, now abandoned, which is a division of application No. 11/713,181, filed on Mar. 2, 2007, now Pat. No. 9,037,230.

(60) Provisional application No. 60/778,740, filed on Mar. 3, 2006.

(51) Int. Cl.
   *A61K 38/14* (2006.01)
   *A61M 5/19* (2006.01)
   *A61M 5/20* (2006.01)

(56) References Cited

U.S. PATENT DOCUMENTS

| | | | |
|---|---|---|---|
| 6,528,315 | B2 | 3/2003 | Bureau et al. |
| 6,763,264 | B2 * | 7/2004 | Hofmann ............... C12M 35/02 604/21 |
| 7,109,179 | B2 | 9/2006 | Roth et al. |
| 7,157,079 | B2 | 1/2007 | Nielsen et al. |
| 7,537,590 | B2 | 5/2009 | Santini et al. |
| 7,769,440 | B2 | 8/2010 | Hoff et al. |
| 8,209,006 | B2 | 6/2012 | Smith et al. |
| 9,037,230 | B2 | 5/2015 | Goldfarb et al. |
| 2002/0119519 | A1 * | 8/2002 | Ebner .................... G01N 33/68 435/325 |
| 2003/0109478 | A1 | 6/2003 | Fewel et al. |
| 2004/0009895 | A1 * | 1/2004 | Varadhachary ......... A61P 37/04 514/19.5 |
| 2004/0014645 | A1 | 1/2004 | Draghia-Akli et al. |
| 2005/0054594 | A1 | 3/2005 | Zhang et al. |
| 2005/0054969 | A1 | 3/2005 | Hoff et al. |
| 2005/0063058 | A1 * | 3/2005 | Langley ............. G02B 27/0006 359/819 |
| 2006/0024358 | A1 | 2/2006 | Santini et al. |
| 2007/0088345 | A1 | 4/2007 | Larson et al. |
| 2008/0075718 | A1 | 3/2008 | Colson et al. |
| 2008/0091135 | A1 | 4/2008 | Draghia-Akli et al. |

FOREIGN PATENT DOCUMENTS

| | | |
|---|---|---|
| JP | 2003-525912 A | 9/2003 |
| JP | 2005-087519 A | 4/2005 |
| JP | 2005-518904 A | 6/2005 |
| WO | WO 1999/06101 A1 | 2/1999 |
| WO | WO 1999/37538 | 7/1999 |
| WO | WO 2003/075978 A2 | 9/2003 |

OTHER PUBLICATIONS

EPO Communication pursuant to Article 94(3) EPC for EP Patent Application No. 07 751 8652 mailed Jun. 28, 2017.
European Search Report for European Patent Application No. 07751865.2, mailed Dec. 20, 2011.
Hanna et al., "Intramuscular electroporation delivery of IL-12 gene for treatment of squamous cell carcinoma located at distant site" Cancer Gene Therapy (2001) 8:151-157.
Heller et al., "Treatment of cutaneous and subcutaneous tumors with electrochemotherapy using intralesional bleomycin," Cancer. Jul. 1, 1998;83(1):148-57.
Javorovic et al., "RNA transfer by electroporation into mature dendritic cells leading to reactivation of effector-memory aytotoxic T lymphocytes: a quantitative analysis" Molecular Therapy (2005) 12(4):734-743.
JPO Office Action for Japanese Patent Application No. 2008-557341, mailed Jan. 31, 2012.
Kashida et al., "In vivo electroporation-mediated transfer of interleukin-12 and interleukin-18 genes induces significant antitumor effects against melanoma in mice" Gene Therapy (2001) 8(16):1234-1240.
Li et al., "Regression of tumours by IFN-a electroporation gene therapy and analysis of the responsible genes by cDNA array", Gene Therapy (2002) 9:390-397.
Li et al., "Regression of tumour growth and induction of long-term antitumour memory by Interleukin 12 electro-gene therapy" CancerSpectrum Knowledge Environment—J. of the National Cancer Institute (2002) 94(10):762-768.
Matsubara et al., "Combinatory anti-tumor effects of electroporation-mediated chemotherapy and wild-type p53 gene transfer to human esophageal cancer cells," Int J Oncol. Apr. 2001;18(4):825-9.
Sersa et al., "Electrochemotherapy with Cisplatin: potentiation of local Cisplatin antitumour effectiveness by application Df electric pulses in cancer patients" European J. of Cancer (1998) 34(8):1213-1218.
Shimizu et al., "Electrochemotherapy for digital chondrosarcoma," J Orthop Sci. 2003;8(2):248-51.
Snoj, M., et al. "Successful Sphincter-Saving Treatment of an Anorectal Malignant Melanoma with Electrochemotherapy, Local Excision and Adjuvant Brachytherapy," Anticancer Drugs. Mar. 2005;16(3):345-8.
Spugnini et al., "Rational design of new electrodes for electrochemotherapy," J Exp Clin Cancer Res. Jun. 2005;24(2):245-54.
Spugnini et al., "Intraoperative versus postoperative electrochemotherapy in high grade soft tissue sarcomas: a preliminary study in a spontaneous feline model," Cancer Chemother Pharmacol. Feb. 2007;59(3):375-81. Epub Jun. 29, 2006.
Tamura et al., "Intratumoral delivery of interleukin 12 expression plasmids with in vivo electroporation is effective for colon and renal cancer" Human Gene Therapy (2001) 12(10):1265-1276.

* cited by examiner

METHOD AND DEVICE FOR TREATING MICROSCOPIC RESIDUAL TUMORS REMAINING IN TISSUES FOLLOWING SURGICAL RESECTION

RELATED APPLICATIONS

This application is a continuation of U.S. patent application Ser. No. 15/488,288, filed Apr. 14, 2017, allowed, which is a continuation of U.S. patent application Ser. No. 13/278,721, filed Oct. 21, 2011, which is divisional of U.S. Patent Application Ser. No. 11/713,181, filed Mar. 2, 2007, now U.S. Pat. No. 9,037,230, which claims the benefit, under 35 U.S.C. § 119 (e), of: U.S. Provisional Patent Application No. 60/778,740, which was filed on Mar. 3, 2006, each of which is incorporated herein by reference.

FIELD OF THE INVENTION

This invention relates to electroporation systems, devices and methods of using such devices for treating tissues surrounding sites of tumors. More specifically, this invention relates to the debulking of tumor masses, sparing of tissue surrounding tumors and reducing tumor mass size and recurrence rates by treating apparently non-cancerous tissues with electroporative pulses and anticancer agents.

Background of the Invention

The following description includes information that may be useful in understanding the present invention. It is not an admission that any such information is prior art, or relevant, to the presently claimed inventions, or that any publication specifically or implicitly referenced is prior art.

Except for vascular disease, cancer is the most frequent cause of death in industrialized countries. The traditionally accepted paradigm for treating cancers and tumors that comprise a single relatively well defined tissue mass has included the use of radiation and chemotherapy typically in association with surgical removal. In cases where surgical resection is an option, surgery is usually the most effective form of treatment. However, the effectiveness of surgical treatment depends on the complete removal of malignant tissue, encompassing the main tumor mass as well as branches and micrometastases which are frequently present in the vicinity of the main tumor.

When removing the main tumor, the surgeon also attempts to eliminate such local or regional micrometastases by resecting apparently normal tissue surroundings the tumor. That tissue is referred to as "margin tissue" or simply as "margin." To what extent margin tissue is removed is subject to the surgeon's judgment. Typically, a margin of 0.5-2 cm around the entire tumor is acceptable. However, more extensive resections are not uncommon for invasive tumors. Even after careful resection of the tumor and margin, most types of tumors recur with a frequency of 10-40%. The recurrence rate depends on multiple factors including tumor size, type and location of the tumor, condition of the patient, etc. In order to reduce the rate of recurrence, surgery is usually followed by radiation and/or chemotherapy. Despite such secondary treatments recurrence rates are still uncomfortably high.

In addition to surgery and radiation, other methods of local tumor control are in use. These include Radiofrequency (RF) Ablation, Photodynamic Therapy (PDT), Cryotherapy (CRYO), Chemo-Radiation (CR), Brachytherapy (BT), Galvanotherapy (GT), and others. Surgery, RF, PDT, CRYO and CR rely on the complete removal or destruction of the tumor and margin tissues, whereas radiation, BT, and GT leave treated normal tissue more or less intact, although radiation and BT may cause severe scarring, fibrosis and vascular and neural damage. In any event, removal, scarring, and physical damage of healthy tissue can result in substantial disfigurement and substantial loss of physical use of body parts and/or functionality thereof. For example, most of the above listed current adjuvants to surgery for destroying or removing tumor masses cause nonspecific damage to normal tissues surrounding the tumor. Excision of a tumor mass can be completely debilitating to function where tumors must be removed from organs including the tongue, vocal chords, rectum, labia, penis, or to fine muscle and visual structures of the face tissue.

To avoid such disfigurement and preservation of function and to ensure that tissues surrounding the tumor are cleared of such cancerous cells, the present invention is provided as an adjuvant or neo-adjuvant to surgery as there is still a need in the oncology arts for a device and method of sparing apparently healthy tissues that lie adjacent to tumors and to reduce tumor mass, growth of the tumor, and recurrence rates.

SUMMARY OF THE INVENTION

In a first embodiment, the invention comprises a method of reducing the probability of recurrence of cancer cell growth in a tissue. In a preferred embodiment, the method includes providing to the cells of said tissue both an electroporating pulse of electric energy and a medicament. In a related embodiment the medicament is preferably provided to the tissue immediately prior to or simultaneously with the electroporating pulse.

In a second embodiment, the invention comprises a method of treating residual cancerous cells remaining in tissues following surgical resection. Preferably, the invention provides for controlling further spreading of cancer by subjecting microscopic nodules or other forms of cancerous tissue to the medicament in an electroporating electric field. In a related embodiment, such treatment can be an adjuvant to surgery in that it can be applied either prior to or after tumor removal. In some circumstances, especially where the cancerous cells have not yet formed into a fibrous mass, no surgical procedure may be employed. In such case, the EP treatment provides a method to reduce tumor mass and terminate or delay further growth of cancerous cells in the tissue. In still a further related embodiment, the invention methods provide for debulking of larger tumor masses by causing through the effect of an anticancer agent, such as Bleomycin, a 'softening' of the tumor tissue such that the tumor mass will be easier to remove from surrounding healthy or normal tissue.

In a third embodiment, the invention method provides for decreasing the amount of normal tissue surrounding a tumor site, i.e. the "margin" tissue, that must be removed at the time of tumor excision and thereby spare normal tissue and consequently provide for greater retention of tissue function, and appearance.

In still other embodiments, the invention provides an instrument that is capable of providing said electroporating energy pulses to the tissue surrounding an excised tumor on demand and in an easily operable manner. In related embodiments, the invention device provides for both administration of an anti-cancer agent and administration of electric fields sufficient to cause electroporation of the tissues in the margin region. Further embodiments of the invention device are provided below.

Other features and advantages of the invention will be apparent from the following drawings, detailed description, and appended claims.

BRIEF DESCRIPTION OF THE DRAWINGS

FIGS. 3A and C are bright field images for Bleomycin and Saline treated skin tissues, respectively, while FIGS. 3B and C are polarized light images showing Bleomycin and Saline treated skin tissues, respectively.

DETAILED DESCRIPTION OF THE PREFERRED EMBODIMENTS

Figure 1:
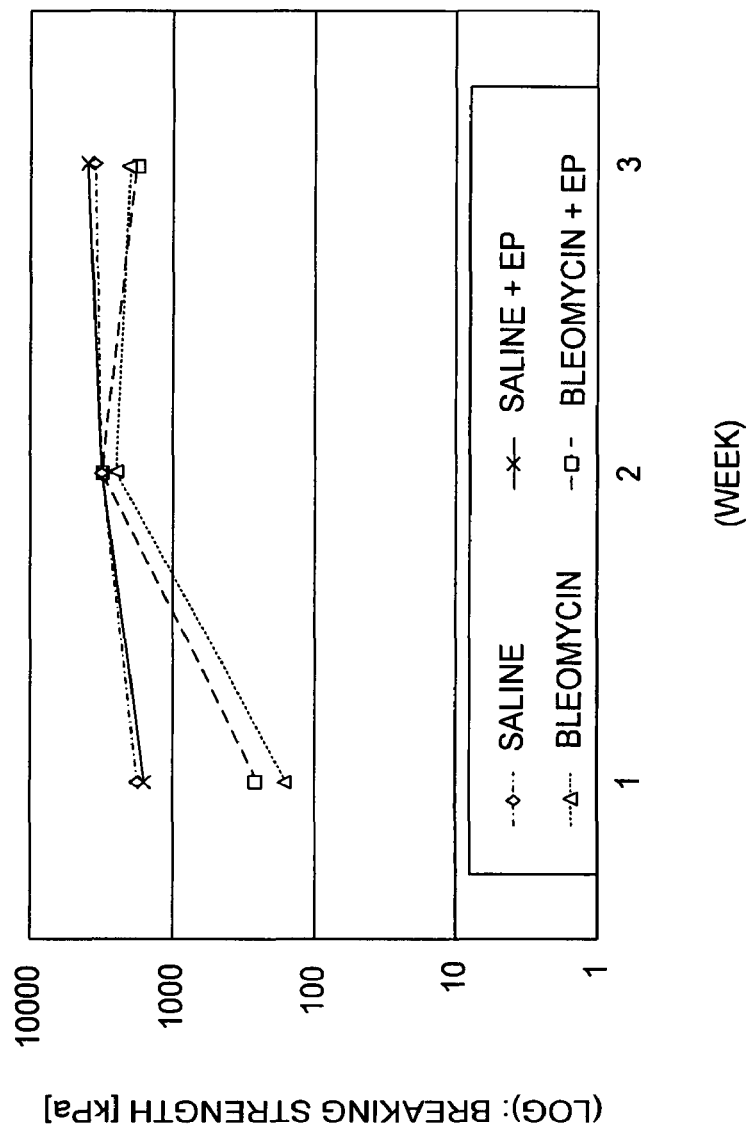
FIG. 1 is a graph showing wound strength as measured by the breaking point of healing skin samples treated in vivo with saline alone, saline plus electroporation, Bleomycin alone, and Bleomycin plus electroporation. Underlying fat and muscle tissue were also treated in these experiments.
Figure 2:
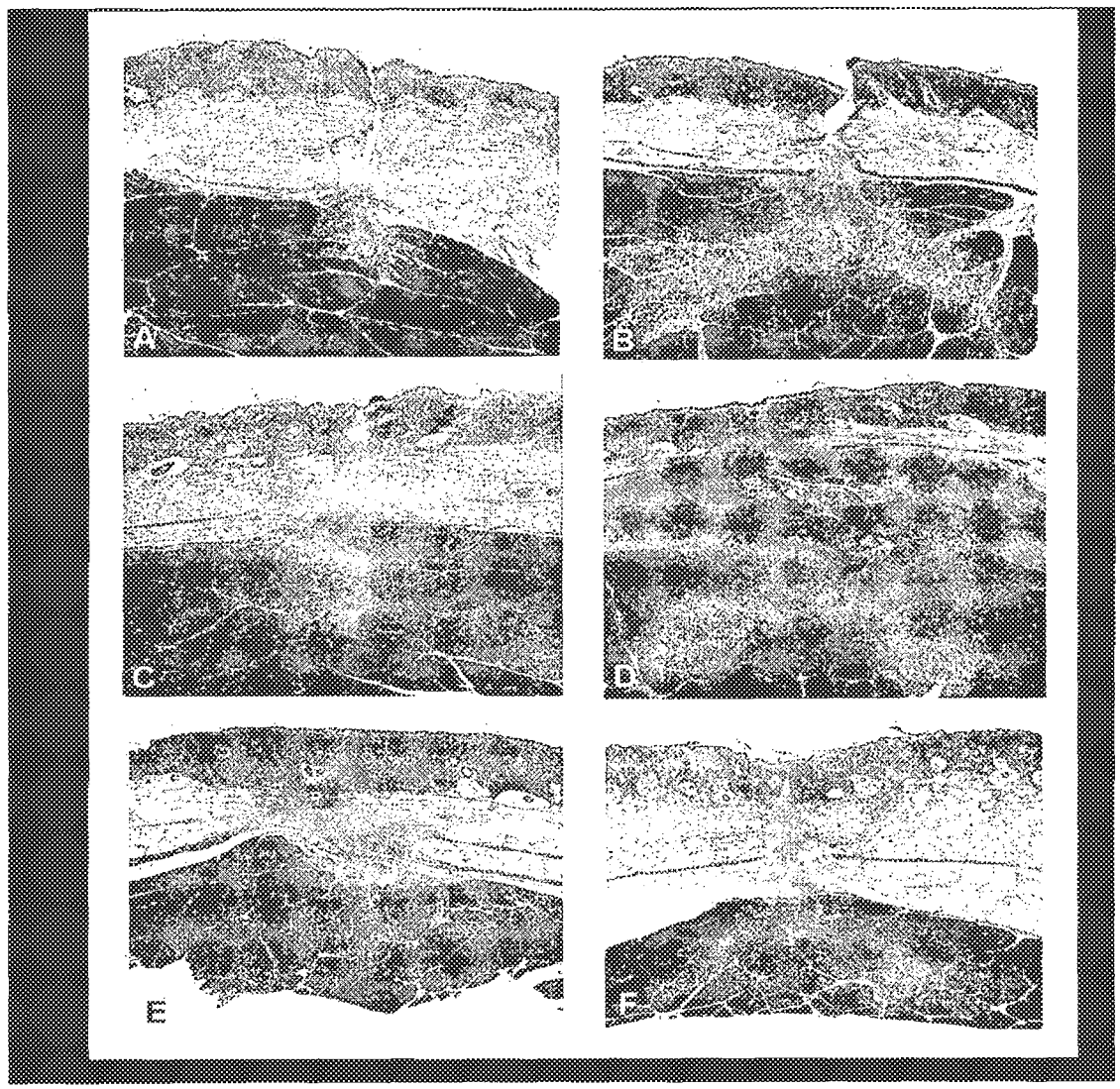
FIGS. 2A-F are micrographs of trichrome stained tissues showing comparisons between (A) untreated tissue at day 2 post incision, and (B) tissue treated with saline plus electroporation at day 2 post incision, (C) saline plus electroporation at week 2, (D) Bleomycin plus electroporation at 2 weeks, (E) saline plus electroporation at 3 weeks, and (F) Bleomycin plus electroporation at 3 weeks.
Figure 3:
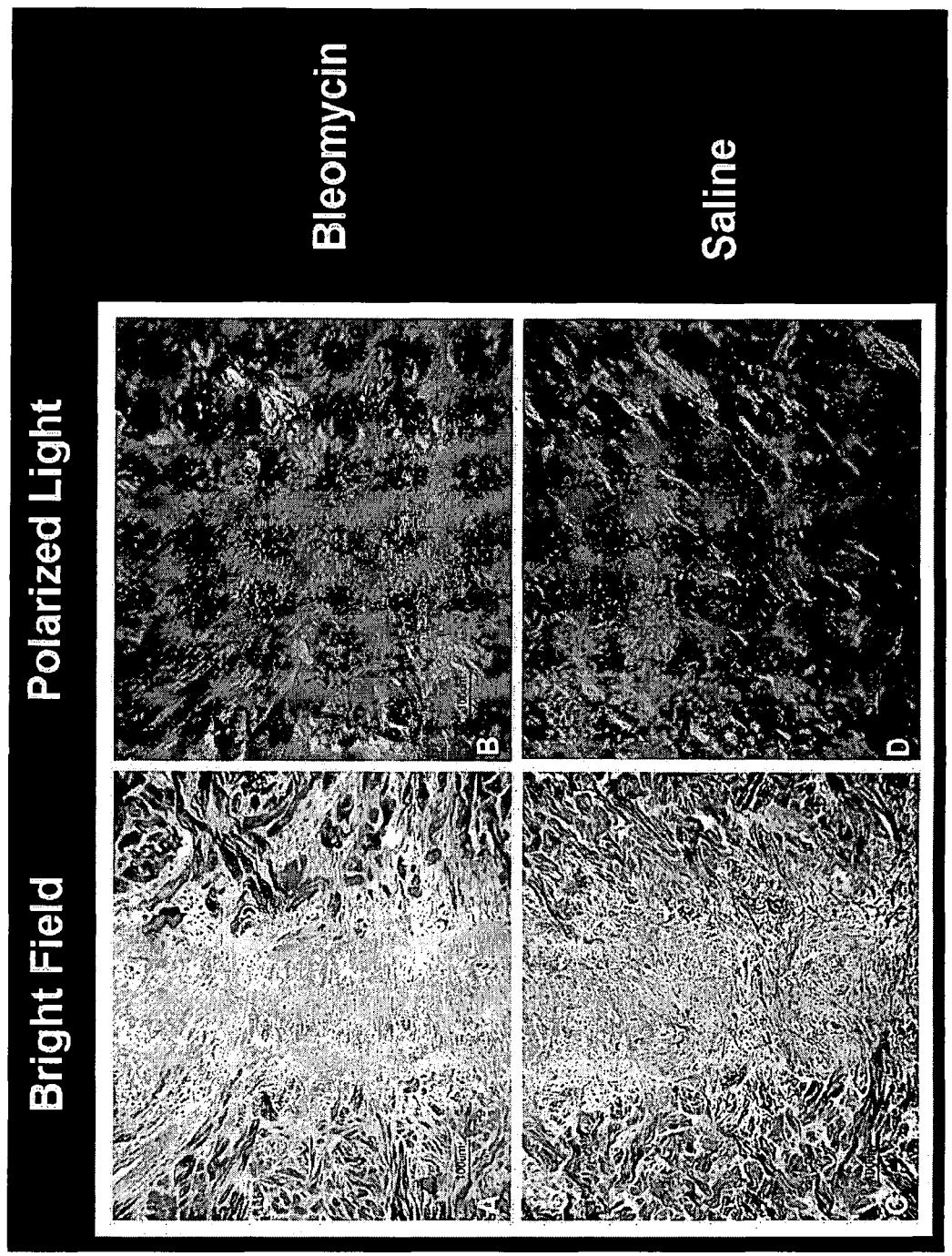
FIGS. 3A-D are stained (Trichrome) micrographs of collagen deposition in skin incisions after three weeks.
Figure 4:
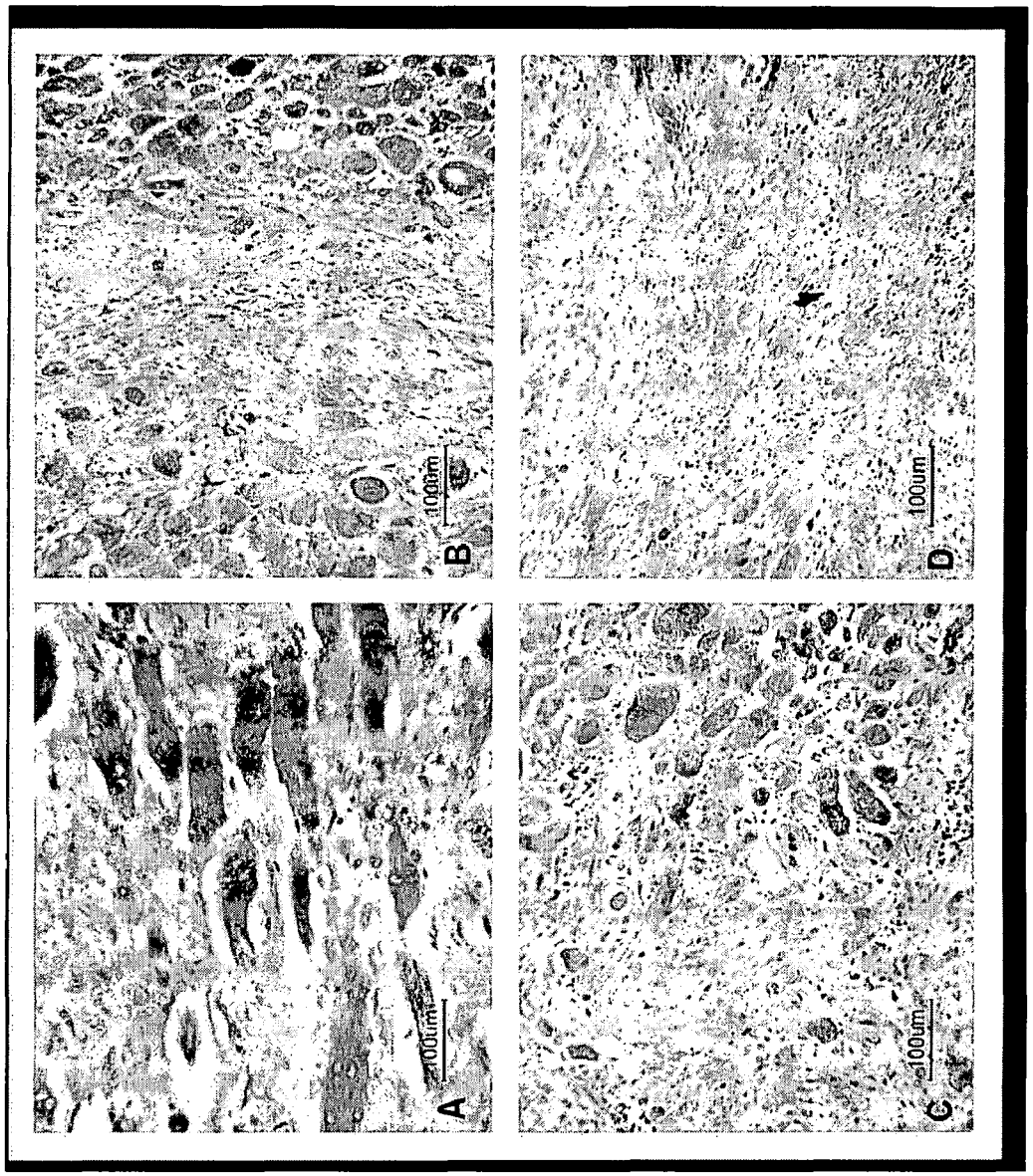
FIGS. 4A-D are micrographs showing samples of muscle tissue at 3 weeks post incision; (A) saline alone, (B) saline plus electroporation, (C) Bleomycin alone, and (D) Bleomycin plus electroporation.

As those in the art will appreciate, the following description describes certain preferred embodiments of the invention in detail, and is thus only representative and does not depict the actual scope of the invention. Before describing the present invention in detail, it is understood that the invention is not limited to the particular device arrangements, systems, and methodologies described, as these may vary. It is also to be understood that the terminology used herein is for the purpose of describing particular embodiments only, and is not intended to limit the scope of the invention defined by the appended claims.

Overview

Electroporation Therapy (EPT), also known as Electro-chemotherapy (ECT), is a method to treat localized cancerous lesions and tumor masses. The method comprises administering certain chemotherapeutic drugs, most commonly Bleomycin, either intratumorally or intravenously. In most cases electroporation (EP) is performed by inserting arrays of needle electrodes and delivering pulsed electrical fields emanating from these electrodes directly to the cancerous cell mass. Pulse parameters are generally within the following ranges: field strength 200-2000 V/cm; pulse length 0.1-10.0 ms; pulse number 2-20; and pulse frequency 1-5 Hz. Applying such electric fields results in permeabilization of tumor cell membranes which allows anticancer drugs to enter cells and to cause up to 5000-fold greater cytotoxicity due to the drug uptake than observed in the absence of electroporation. EPT has been shown to be effective against many types of solid tumors in animals and several types of tumors in humans. In fact, several clinical studies are presently ongoing, including a Phase III study evaluating the safety and efficacy of EPT for the treatment of squamous cell carcinomas of the head and neck. However, such treatment studies are not designed or intended to treat or test the affect of EPT on noncancerous margin tissue coincident to cancerous cells.

EPT is somewhat unique among the many methods employed for local and regional tumor control in that it is far less damaging to normal tissue than to malignant tissue. Results from in vitro as well as in vivo animal and human studies indicate that EPT using a drug, such as Bleomycin, effectively destroys most tumors via apoptotic and necrotic mechanisms while causing only a minor effect (inflammation, minor necrosis) on normal tissues surrounding the tumor, particularly when Bleomycin concentration, doses, and pulse parameters are within appropriate ranges. The margin tissue surrounding tumors that is typically amenable to treatment include, without limitation, those of organs including breast, prostate, tongue, penis, labia, rectum, vocal chords, liver, squamous cell carcinoma of the head and neck (SCCHN), cutaneous and other tumors. EPT can be performed on such tissues whether the tumor mass has been removed or not. In such cancers the patient would be helped substantially by treating the tissues in a manner wherein healing can proceed largely unimpaired and there is a possibility of eliminating microscopic metastases and tumor branches trending into the tissues that give rise to local recurrences. As is also understandable with respect to the invention methods, electroporation treatments with agents such as Bleomycin provide for a measurable degree of selectivity in targeting cancerous cells. This methodology is also pertinent to treatments with other agents that have specific activities against particular disease states, such as highly localized infectious diseases and other disease states where there are foci of infected or diseased tissues wherein a cell, or group of cells that are infected or diseased, can be targeted by the agent to destroy the affected cells. In such case electroporation of such cells and surrounding tissue will allow the agent to reach its intended target in the infected or diseased cells, yet not have a detrimental effect on uninfected or normal cells as empirically observed. The molecular and cellular mechanisms underlying the different response of abnormal and normal cells, respectively, is presently unknown. Additionally, use of the invention methods and device is applicable to disease states where sites of cancerous cells are distributed in areas not easily amenable to surgery. For example, skin tissues of the face containing microscopic or focal disease sites can be treated with the invention device in the same manner as used for treating a margin tissue bed resulting in substantially less scarring than would be caused by surgery. Thus, the invention methods can be used as an adjuvant to surgery or even a neo-adjuvant. Specifically, cells of tumor mass can be electroporated along with surrounding normal tissue and thereby provide for a method of debulking the tumor mass in providing for a mechanism to hinder, terminate or otherwise reduce the growth and/or recurrence rates of the diseased cells. In such case, tumor tissue can be removed either before or after EPT, or can even be allowed to remain unexcised following EPT, in which cases the effect of an agent such as Bleomycin will provide for cell death by apoptotic and/or necrotic mechanisms and softening of the tumor cell mass followed by further necrosis. Normal tissue in the vicinity will remain largely unaffected.

Typically, treatment of a tumor with EPT includes a Bleomycin dose of 1 Unit/ccm tissue to be treated, injected intratumorally at a concentration of 4 Units/ml. The pulsed fields are generated such that the field is usually applied in six separate pulses at 4 Hz, one each in 6 different field orientations, each of 100 usec duration, at a nominal field strength of anywhere between 200 and 2000V/cm but, generally between 600 and 1500 V/cm, more usually between 600 and 1400 V/cm and even more usually between 1200-1300 V/cm across the tumor mass. Increasing Bleomycin dose or concentration and increasing the intensity of the electroporating pulse beyond the standard parameters can result in more severe effects on normal tissue. At very high field strengths and/or pulse lengths EP by itself (i.e., for example, without Bleomycin) can induce irreversible cell membrane deterioration, leading to the destruction of tumor as well as normal cellular tissue falling within the effective electric field. In still further related embodiments, a device for operating the methods of the invention can itself be operated using pulsed field strengths of between 1-600 V/cm when injecting DNA as a therapeutic agent as set forth in U.S. Pat. No. 6,528,315 which reference is herein incorporated in its entirety by reference. In such embodiment, the DNA ideally codes for a polypeptide that provides for a therapeutic anticancer effect on the tumor-containing tissue being treated.

With regard to other agents, including genes, proteins, cytokines, chemokines, steroids, antibodies, RNAi, and antisense nucleic acids, the same high pulsing parameters can be used (i.e., for example, 800-1500 V/cm or, alternatively, 1-600 V/cm, more preferably 200 to 600 V/cm, and still more preferred 400-600 V/cm. It is further contemplated that these and any other agents can be used where such agents promote wound healing without promoting growth of malignant cells. With regard to using such agents in EPT, lower-end field strengths as low as 50V/cm can be used to electroporate cells within tissue containing microscopic lesions and diseased cells where the tissues have not formed an abnormal tissue mass.

As mentioned earlier, the present rationale for cancer therapy involves in one embodiment surgical removal of the tumor mass ('debulking') to reduce biological stress on the patient, surgical elimination of margin tissue to eradicate micrometastases and invading tumor tissue, and radiation and/or chemotherapy to control local, regional and systemic spread of the tumor. While surgical removal of the tumor itself generally provides relief for the patient, without severe sequelae, the subsequent steps of margin resection, radiation and chemotherapy can be very detrimental to the patient. Physiological and mechanical function, look, quality of life and eventual outcome can be severely affected by these treatments. Therefore, it would be ideal to combine surgical removal of the tumor with a treatment method that (a) prevents tumor recurrence due to micrometastases and invasive tumor tissue more effectively than present methods, and (b) minimizes the loss of surrounding margin tissue. In the present invention, a novel application of EPT as a surgical adjuvant or neo-adjuvant is provided to achieve either reduction of tumor mass, prevention of tumor recurrence and minimizing the need to excise margin tissue or both.

Turning now to the invention method, the current invention is intended to provide a novel method for lowering the probability of recurrence of tumor growth in otherwise normal tissues surrounding a site of excised cancerous cells. In other words, the invention method comprises treating "margins" of tissue surrounding a site of cancer cells, such cancerous cells typically formed at a distinct tissue site. In a preferred embodiment, the invention method provides for reducing the amount of tissue that must be excised along with the tumor and its cancerous cells and making radiation or chemotherapy superfluous. The method comprises applying an electroporative pulse of electric energy to the tissues surrounding the tumor site. In addition to the application of an electroporative pulse, the method further comprises providing, preferentially either prior to or simultaneously with the electric pulse, a formulation comprising an anticancer medicament. In a preferred embodiment, such medicament comprises a biologically active molecule. For example, the medicament can comprise a nucleic acid encoding an expressible polypeptide, such as, for example, a nucleic acid in an expression vector and comprising a gene sequence for a cytokine or chemokine, antibody, or enzyme. Another example comprises antisense DNA or RNA, or interfering RNA (RNAi). Alternatively, the medicament can comprise a polypeptide or an organic molecule such as, for example, a cytokine, chemokine, antibody, Cisplatin or Bleomycin, or any other molecule having an anticancer activity. Further, any of such compounds disclosed above can be administered in a formulation that can comprise any combination of pharmaceutically acceptable salts, buffers and other excipients as are well known in the art. For example, formulations for nucleic acids can comprise, for example, said nucleic acid and poly-glutamic acid (poly-L-glutamate) as described in U.S. Pat. No. 7,173,116 herein incorporated in its entirety by reference.

In a further embodiment, the invention method comprises applying the electroporative pulse using a device capable of providing such electroporative pulses to localized areas at the tumor site. In a preferred embodiment such a device can include an array of elongate needle-like electrodes. Alternate embodiments can use short non-penetrating electrodes or semi-penetrating microneedle electrodes depending upon the strength of the electric pulse required and upon the delivery mode of anticancer agent. In such embodiment, the device would be designed without a need for a plunger and delivery needles. Instead, the treatment methods can be applied using an electroporation device comprising an electrode array only, such array comprising the non-penetrating or semi-penetrating electrodes. In such a case, drug would be delivered by separate means such as a syringe. In a further preferred embodiment with respect to any of the physical arrangements of the invention device, during performance of the treatment procedure, the electrodes are positionable with respect to the tissues to be treated to create an electric field having a field strength and energy sufficient to electroporate cells in said tissue within a specified area and depth. Typically, the device will be positioned to impart an electroporative pulse to all tissues within a preselected margin of tissue around (in three dimensions) the tumor excision site. Depending upon the size of the excised tumor and the size of the electrode array, the surrounding margin tissue bed can be electroporated either entirely in one electroporative pulse application or may require a multiplicity of electroporative pulse applications by the positioning and repositioning of the electrode array so as to completely encompass the tumor site margin tissue in electroporating energy fields. In some embodiments, the electrodes can serve as delivery needles for the agent intended to be electroporated into the cells, while in other embodiments, the agent can be administered to the tissue independently from the administration/positioning of the electrodes in the tissue.

Additionally, in order to be sure that the invention method is capable of exposing healthy non-cancerous tissues to electroporative pulses without substantially damaging said healthy tissues, a study was conducted on the recovery characteristics of healthy tissue surrounding an open wound after exposure to electroporative pulses. As disclosed below, treatment of healthy tissues with electroporative pulses, or electroporative pulses and an anticancer agent, imparted no measurable significant effect to the cells of the treated area and the open wounds healed similar to untreated and/or normal tissues. Since healthy tissues can be exposed to an electroporative pulse without substantial detriment, use of electroporation in the treatment of tissues surrounding a tumor for the purpose of allowing surgeons to excise a narrower margin of healthy tissue is now possible.

General Treatment Procedure

One embodiment of the invention methods is to treat surgical wound margins or, more generally, tumor margins and in the process (a) achieve a superior recurrence rate (i.e., less frequent recurrence) compared with conventional surgical tumor and margin resection with or without secondary treatment; (b) reduce or eliminate the need for surgical resection of margin tissue while maintaining equal or better recurrence rates as with traditional surgical margin removal, and thus preserve functional tissue; and (c) reduce or eliminate the need for radiation or chemotherapy subsequent to surgical tumor resection (with or without margin resection) while maintaining equal or superior recurrence rates as with traditional surgical margin resection and secondary treatments such as, e.g., radiation, and chemotherapy.

The following examples are intended to illustrate but not limit the invention. While they are typical of those that might be used, other procedures known to those skilled in the art may alternatively be used.

Example I

Treatment of Apparently Healthy Tissue Surrounding an Open Wound with Electroporation Pulses and/or Anticancer Agent In order to successfully use electroporation in areas of open wounds comprising for the most part normal tissue, we conducted a series of experiments to show that electroporation of normal tissue, with or without anti-cancer agent, can be performed without significantly affecting the healing processes in cutaneous, subcutaneous and muscle tissues.

In this experiment eighteen transcutaneous incisions were made into the dorsal muscles in each of eight pig test animals grouped 1-6. In study groups 1-5, longitudinal incisions were made while in group 6 the incisions were transverse to the longitudinal orientation of the muscle fiber. At each incision site, either nothing, normal saline, or Bleomycin in solution was injected such that injections were placed to a 1 cm depth and spaced at 1 cm distances from one another with three injections, one on each side of each incision within 3 cm of each other and one in the center of the incision. Bleomycin, an anti-cancer agent, was used wherein each injection consisted of 0.125 ml (4 units/ml saline). The incisions were then treated with bipolar pulses of 530 V, 100 usec each, from a pulse generator using a 6-needle electrode array of 0.5 cm diameter (nominal field strength for each pulse was 1,233 V/cm).

Specifically, 8 male Yorkshire/Hampshire cross swine (40-50 kg) were acclimated 5-7 days prior to surgery. Incision locations were marked on the dorsum using sterile surgical markers. Each incision was 5 cm long and made to a depth of 5 mm into the muscle. All animals in groups 1-5 received 18 longitudinal incisions each, while animals in group 6 received transverse incisions, in accordance with Table I. Each study group comprised 24 incisions.

TABLE I

| Group | Incision | Injection | Electroporation |
| --- | --- | --- | --- |
| Group 1 (NL) | Longitudinal | None | |
| Group 2 (SL) | Longitudinal | Saline | |
| Group 3 (SEL) | Longitudinal | Saline | X |
| Group 4 (BL) | Longitudinal | Bleomycin | |
| Group 5 (BEL) | Longitudinal | Bleomycin | X |
| Group 6 (BET) | Transverse | Bleomycin | X |

Injections of a total volume of 1.5 ml of saline or Bleomycin (6 U) were administered at 12 sites per incision, 6 in the muscle and 6 in the skin. Incisions treated with electroporation were electroporated using a 0.5 cm diameter, 1.5 cm long needle array. On each side of the muscle incision, electroporation was given 3 times in the central 3 cm of the incision, each electroporation site being 1 cm apart from the other. Skin was not electroporated. The epimysium was closed with 4-0 Vicryl absorbable interrupted sutures. The skin was closed with 4-0 nylon interrupted sutures. Swine were sacrificed at 2 d, 1 wk, 2 wks, or 3 wks following surgery. Histology specimens containing skin and at least 5 mm depth of underlying muscle were taken from the center of the incision and immediately placed in 10% neutral buffered formalin. An additional control specimen was taken from non-incised skin on the dorsum. After staining and sectioning, skin, subcutaneous tissue, and muscle were graded histologically on a 0-3 scale using the following parameters: Healing, Granulations/Fibrosis, PMN's, Lymphocytes, Histiocytes, Necrosis, Hemorrhage and Atypical Cells.

Mechanical testing was performed on strips of skin removed from the center of the incision at three different time points, namely, Days 7, 14, and 21. Skin strips were wrapped in gauze soaked in saline and tested the same day for incision breaking strength using an Instron 900 (Instron Corp. Norwood, MA) with a 100 pound load cell run at 0.5 in/min. Breaking strength was determined by plotting the stretch versus the strain for each incision up to the breaking point. Breaking strength of skin incisions increased over time in Group 1 (no saline or Bleomycin) from ~1800 kPa at 1 week to ~2500 kPa at 2 weeks and ~5000 kPa at 3 weeks post-incision. Injecting saline (Group 2) yielded similar results. Group 3 (saline injection with electroporation) was not significantly different from Group 2 at any time indicating that electroporation did not cause adverse effects in breaking strength. At 1 week, all three Bleomycin treated groups had significantly (i.e., 90%) reduced breaking strengths compared to all three non-Bleomycin groups, indicating that Bleomycin had delayed dermal wound healing. Electroporation had no adverse effects on breaking strength as Groups 4 and 5 were not significantly different from each other. By week 2, there were no significant differences between Groups 1-5. Only the transverse incisions with Bleomycin and electroporation exhibited lower breaking strengths. This effect carried through to week 3 where Group 6 had significantly lower breaking strength than Groups 1-5.

As shown in FIG. 1, there was no substantial difference between saline alone, saline plus electroporation, Bleomycin alone, or Bleomycin plus electroporation after three weeks post incision. Even the strength of healed transverse incisions is sufficient not to be of clinical concern in terms of risk to the patient.

Histological Evaluation

Histology specimens at four different time points, namely, Days 2, 7, 14, and 21 containing skin and at least 5 mm of muscle were taken from the center of the incisions and immediately placed in 10% neutral buffered formalin. Histological studies showed statistically significant changes (Bleomycin groups only) present at day 7. All non-treated tissue and saline injected tissue remained normal in appearance. By day 21, all Bleomycin injected samples were comparable with saline-injected controls. For example, when comparing saline-injected v.s. saline-injected plus electroporated tissue samples, the only effects of electroporation were slight increases in the number of skin histiocytes at 1 week and a reduction in skin lymphocytes at 2 weeks. There were no effects of electroporation on any of the other parameters such as healing of skin, subcutaneous tissue and muscle. Further, when comparing Bleomycin v.s. Bleomycin plus EP treated tissue samples there were no significant differences at 2 days or 1 week. At 2 weeks, electroporation caused a significant increase in muscle necrosis but that difference disappeared by 3 weeks. At 3 weeks electroporation caused a reduction in skin histiocytes but showed increased granulation tissue/fibrosis in the muscle, evidence of healing. There were no sustained significant differences in healing of skin, subcutaneous tissue or muscle caused by electroporation even in the presence of Bleomycin.

As shown in FIGS. 2A-F, wound healing as compared between untreated tissue, saline plus electroporation treated tissue, and Bleomycin plus electroporation treated tissue, becomes histologically equivalent by week three. Specifically, by week three saline plus electroporation is equivalent to Bleomycin plus electroporation (compare E and F). By week 2 saline plus electroporation shows more advanced healing than Bleomycin and electroporation (compare C and A). By week 3 saline plus electroporation appears equivalent to Bleomycin plus electroporation at week 2 (compare E and D).

With regard to other histological features as shown in FIGS. 3A-D, collagen is deposited in the healing wound but maybe at a slower rate for Bleomycin treated samples than samples treated with saline. Specifically, with no electroporation, incisions in saline treated animals (C and D) show deep blue collagen fibers in continuity with the collagen fibers of the dermis while incisions of Bleomycin treated animals (A and B) show pale blue collagen fibers with fewer zones of continuity with the dermal collagen. With respect to effect, if any, on the muscle tissue, as shown in FIGS. 4A-D, at 3 weeks the micrographs indicate that electroporation does not cause significant differences in the healing of muscle tissue compared to saline or Bleomycin alone.

Considering the effect, if any, of longitudinal vs transverse incisions, in the presence of saline vs Bleomycin, there were no significant differences at 2 days or 1 week. At 2 and 3 weeks the only significant histological differences were in the amount of granulation tissue/fibrosis at all three tissue layers studied. In skin, subcutaneous tissue and muscle, longitudinal incisions had more granulation tissue/fibrosis than transverse incisions in every case where there were significant differences. This is expected as longitudinal incisions generally heal better than transverse incisions. The scores for healing of skin, subcutaneous tissue and muscle were not significantly different for longitudinal and transverse incisions.

SUMMARY

Electroporation of the muscle caused no significant alteration in the breaking strength of porcine dermis in the presence or absence of Bleomycin at weeks 2 and 3 and arguably even within week 1. However, the presence of Bleomycin regardless of whether EP was used, was associated with a reduction in the breaking strength of porcine dermis up to 1-2 weeks post treatment when compared to incision only, or to incision injected with saline, with or without EP. With respect to histology, electroporation of the tissues resulted in no significant differences in healing of the skin, subcutaneous tissue or muscle. Thus, electroporation therapy does not significantly adversely affect healing of muscle or skin. This appears to apply also where EPT is used for treatment of tissue surrounding tumors, and thus the methods of the invention provide an alternative to surgical resection or other therapeutic interventions in the treatment of wound margins aimed at reducing tumor recurrence.

Example II

Hypothetical Treatment Regimen

It is contemplated that surgery using the invention method and device will generally follow a protocol likely to employ the following steps:

1. The main tumor mass will be surgically resected as usually practiced by a surgeon skilled in the art. The surgeon will either resect the primary tumor mass only or will also resect a surgical margin. Alternatively, the main tumor may be ablated by one of many ablative therapies, such as RF (radio frequency) ablation, PDT (photodynamic therapy), cryotherapy, chemo-radiation, brachytherapy, or even galvanotherapy, with or without ablation of margin tissue.

2. After surgical resection (or ablation) of the tumor mass, with or without resection (or ablation) of margin tissue, the entire tissue surrounding the resection (or ablation) site will be treated by EPT employing Bleomycin or other chemotherapeutic or biological drugs. Drug-EPT treatment will be performed to a depth as determined by the surgeon according to theoretical considerations, scientific studies, or practical experience.

Variation A. Protocol for Resecting a Tumor with Standard Margins

1. In this protocol variation, after the tumor has been removed along with standard margins, the entire wound surface (tumor margin bed) is treated to an appropriate depth, typically 1 cm with a standard EPT regimen typically comprising local injection of an anticancer agent followed by electroporation using at least a multi electrode array equipped device (for example, a six needle array or other electrode arrangement of an invention device such as disclosed in FIGS. 5-10) and, for example, pulsing in at least three field orientations with an appropriate voltage. By field orientations is meant the spatial and directional orientation of the electric field generated by the electric pulse between any two oppositely charged electrodes. In this embodiment, the protocol Variation A can be performed without the use of (or alternatively a reduced use of) traditional post-surgical secondary treatment. In such instance, the invention method is intended to achieve equal or better recurrence rates compared to complete surgical margin resection and secondary treatment.

2. Following EPT of the tumor margin bed, if desired, the patient can be further treated with conventional secondary treatment, such as radiation or chemotherapy, and thereby provide additional potential protection against tumor recurrence compared with no EPT treatment of the margin tissues.

The outcome of performing steps 1 and 2 above is intended to comprise improved cure rate or time to recurrence with some degree of preservation of tissue over conventional therapies but margin tissue would have been removed nonetheless.

Variation B. Protocol for Resecting a Tumor with No Margin Resection

1. In this protocol Variation method, following tumor removal and reduced or no margin removal, the entire wound surface is treated to an appropriate depth, typically 1 cm with a standard EPT regimen typically comprising local injection of an anticancer agent followed by electroporation using a multi electrode array (for example, a six needle array or an array as disclosed in the attached figures) and, for example, pulsing in at least three field orientations with an appropriate voltage.

2. The intended outcome following this protocol and additional conventional secondary treatment is complete or partial preservation of margin tissue and potentially improved cure rate or time to recurrence.

In alternate embodiments of the above protocols, no traditional secondary treatment is provided, yet the intended outcome is complete or partial preservation of margin tissue and improved cure rate or time to recurrence.

Example III

Turning now to a disclosure of an electroporation device suitable to treat margin beds of resected tumors, in a first embodiment the device is intended to provide the capability to deliver to the margin tissue an anticancer agent, e.g., for example, Bleomycin, evenly distributed throughout the margin bed. In a second embodiment, the device provides for the capability of delivering to the margin tissue a plurality of pulses of electric energy sufficient to cause electroporation of cells throughout the margin bed to a depth of between 1 and 1.5 cm.

In a third embodiment, the invention device can provide for delivery of the electroporation pulses to a substantial portion of the margin bed, if not all of the margin bed (depending upon the relative dimensions of the device and the tumor), by a single placement of the invention device such that in order to provide electroporating pulses to the entire margin bed the device should preferably only need to be placed once.

In further embodiments, the device includes a plurality of electrodes positioned in a geometric array to provide for delivery of a series of electric pulses between selected electrodes of the array. In a related embodiment the device can comprise a plurality of shapes to accommodate various tumor shapes and sizes and further provide an array of electrodes in a preferred geometry.

In still other embodiments, the electrodes of the invention device can comprise elongate hollow needles such that the electrodes can act as both electrodes and anticancer agent delivery needles. In a particularly preferred embodiment, the invention device can include a sharps cover to cover the electrodes and to provide a mechanism for delivery of anticancer agent to the hollow needles and a means for keeping the electrodes sterile prior to surgery.

Figure 5:
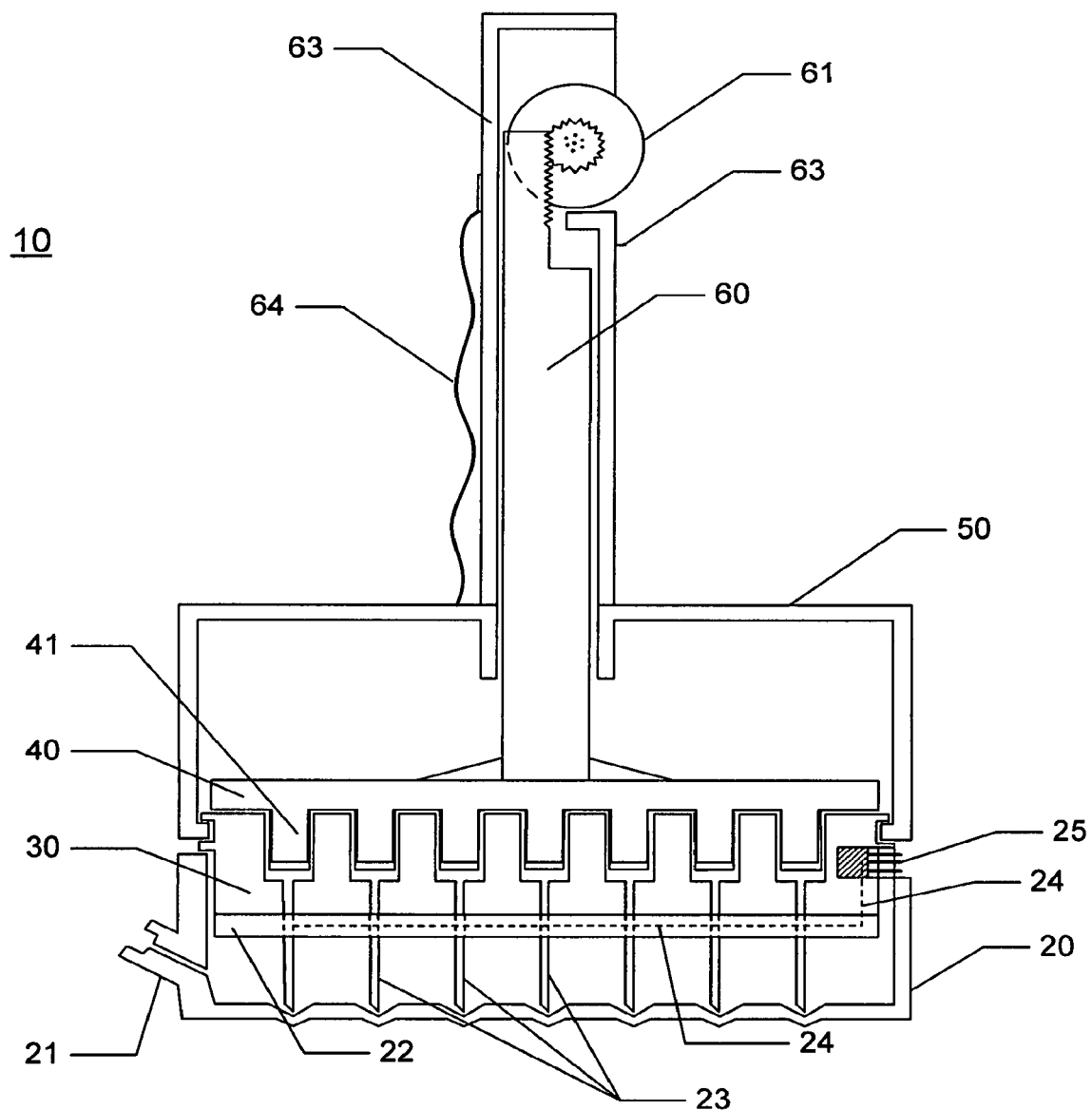
FIG. 5 is a cross sectional figure of one embodiment of the invention device showing an embodiment comprising a handle comprising a thumb wheel for raising and lowering an array of plungers which actuate loading or dispensing of a substance through the electrode needles.

Turning now to specific details of the invention device, FIG. 5 shows invention device 10 comprising a substantially rigid sharps cover 20 which doubles as a therapeutic agent filling tray. The cover/tray 20 further comprises a fill port 21 which can be designed with a fitting capable of connecting with any desired type fitting for attaching to a source of fluid for filling the tray to a desired level of therapeutic substance. The cover/tray 20 snuggly fits the main body of the invention device which itself comprises a substantially rigid substrate 22 through which an array of a plurality of elongate electrodes 23 pass and which are each individually connected to electric leads 24 which terminate on a lateral portion of the device in a plug or connector 25 for attachment to a source of electrical energy. The substrate 22 and the plug 25 are connected to main body substrate 30 which itself comprises an array of a plurality of wells 31 (see FIG.

6). Each well comprises a hollow electrode/needle through which a substance such as a therapeutic substance can be transmitted.

Figure 6:
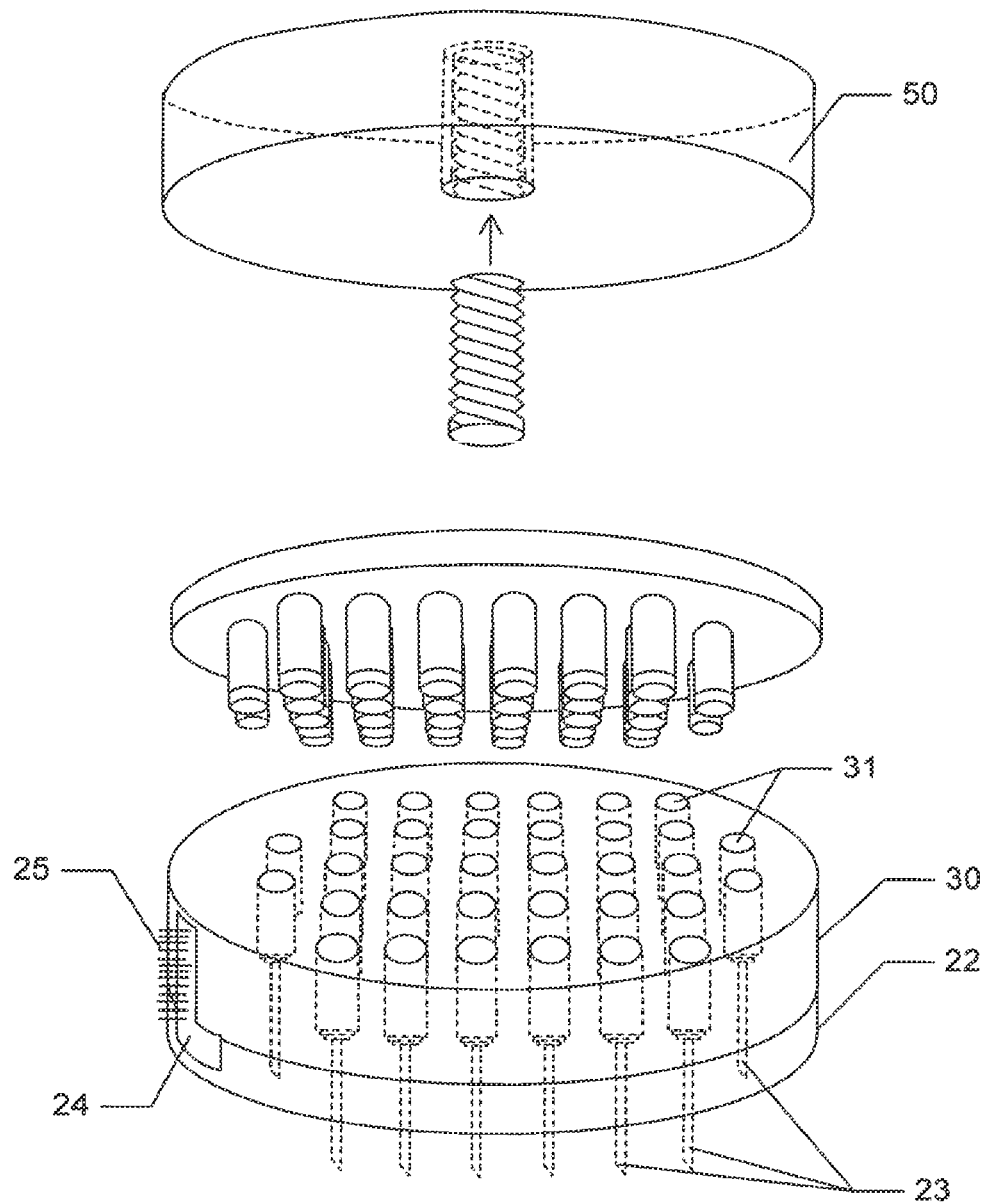
FIG. 6 is a drawing depicting an exploded view of one embodiment of the invention.

Fitting with the substrate 30 is substrate 40 which comprises an array of a plurality of plungers 41. The substrate 40 is connected to a mechanism which can actuate the movement of the substrate 40 towards and away from substrate 30 so as to drive into or extract away from substrate 30 the array of plungers 41 of substrate 40. In one embodiment, the substrate 40 is actuated by a central rod 60 connected to substrate 40 on one end and at the other configured into a ratchet and a thumb activated wheel 61. In a related embodiment, substrate 50 further forms an enclosing support structure 63 to surround and enclose central rod 60. The support structure 63 can further comprise user friendly handgrip 64. In operation, the operator would use port 21 to fill the cover/tray 20 to a desired level with a fluid therapeutic agent, such as for example Bleomycin, then use the thumb wheel 61 to draw into the wells 31 the agent (FIG. 6). The operator would then remove the device from the tray 20 using the handle formed by the support structure 63 and place the device at an appropriate position on the tissue or margin bed. The operator would then insert the electrodes, activate the thumb wheel 61 to administer the agent into the tissue followed by activation of the electrodes, the device having previously been attached to a source of electrical energy via the plug 25.

Figure 7:
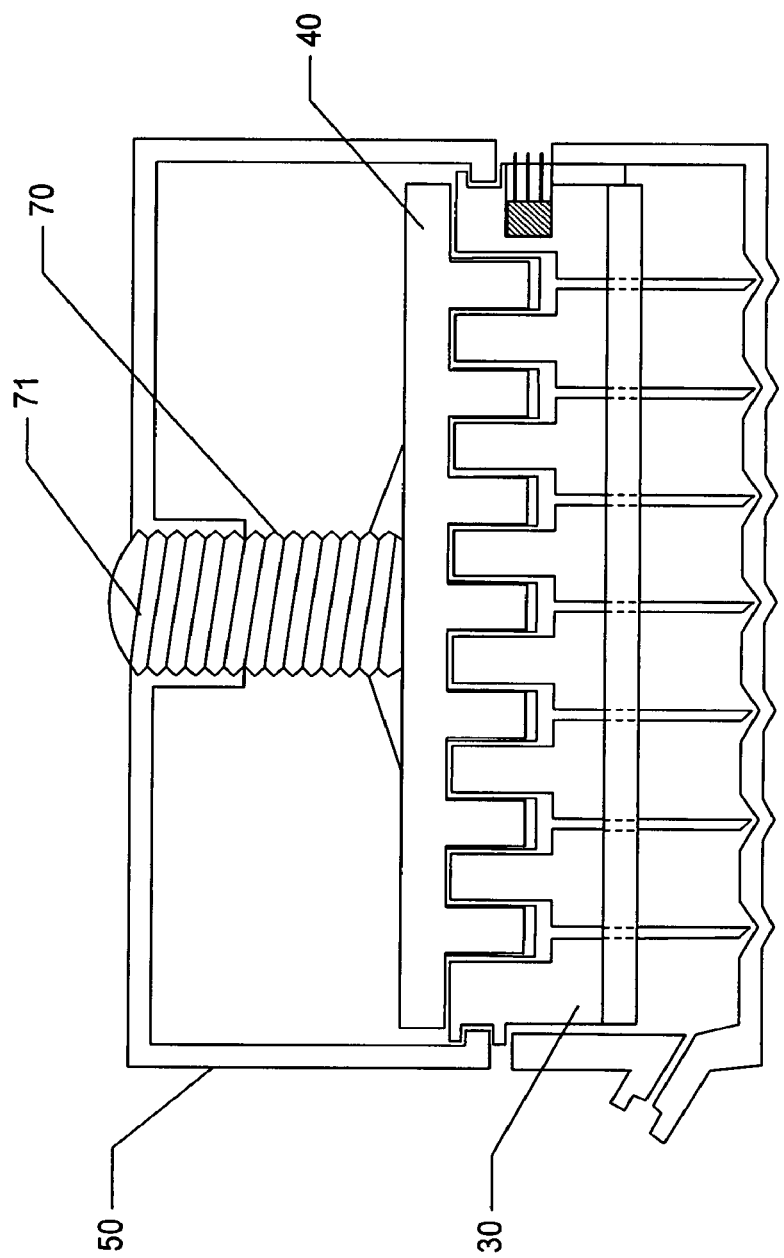
FIG. 7 is a cross sectional drawing of one embodiment of the invention device wherein the plungers are actuated by a screw driven by clockwise (raising plungers) and counter clockwise (lowering plungers) rotation of the housing 50.
Figure 8A:
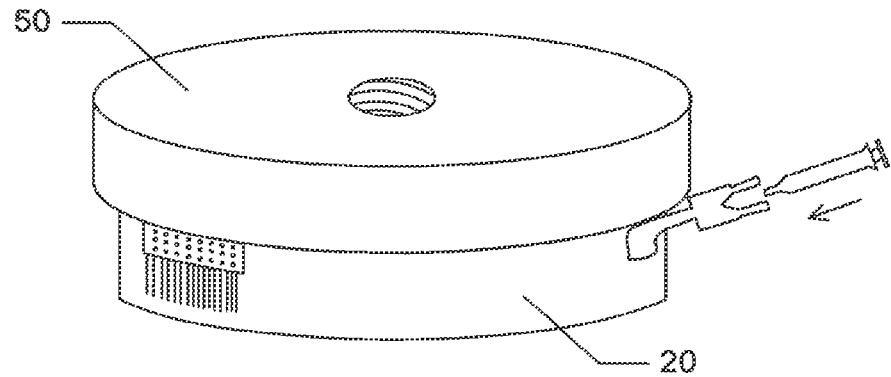
FIGS. 8A and B are perspective drawings of one embodiment of the invention wherein rotation of the housing 50 will drive the array of plungers back and forth. Figure A shows the embodiment with the tray 20 while Figure B shows the main body of the embodiment without the tray 20.
Figure 8B:
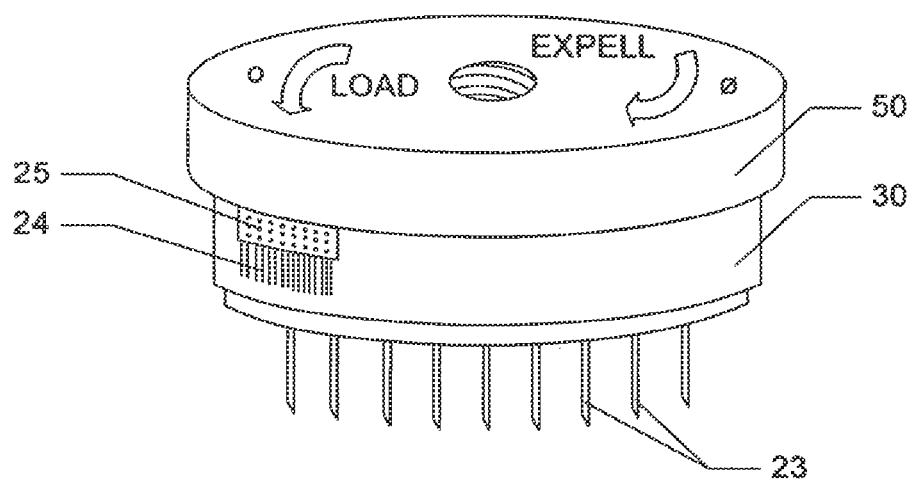
Figure 10:
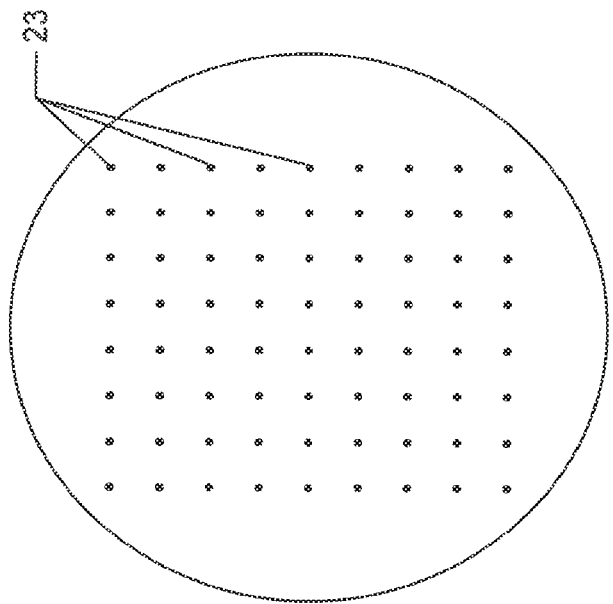
FIG. 10 shows an example of the array of the plurality of electrode needles from the underside of the substrate 22.

The invention device further can comprises other various arrangements of components to provide the same result. For example, in one embodiment the device can comprise attached to the substrate 30, an optionally dynamic housing 50. Housing 50 is considered dynamic on an optional basis since depending upon the style of the invention chosen, the housing can rotate clockwise and counter clockwise to raise and lower the plunger instead of using a thumb wheel. In embodiments such as that depicted in FIG. 5, the housing 50 is not dynamic in that although the housing 50 may be capable of rotation, but for the handle and thumb wheel, such rotation in this embodiment servers no utility. Alternatively, as depicted in FIGS. 7 and 8, the housing is dynamic in that substrate 40 is actuated toward or away from substrate 30 by screw 70 which is attached at one end to substrate 40 and to housing 50 on the other end by engagement of said screw 70. The housing 50 portion which interacts with threads of screw 70 is itself formed into screw threads 71 which upon rotation of housing 50 will draw substrate 40 away from or towards substrate 30. In operation, the operator would fill the cover/tray 20 with agent as previously described, then place the discoid device appropriately on the tissue to be treated. After inserting the electrodes into the tissue, the user would, while pressing down on the device, rotate the housing 50 in the direction that will move the plungers toward substrate 30 and thereby expel the agent into the tissues. The operator would then active the electrodes, assuming the device had been previously connected by plug 25 to a source of electrical energy.

Figure 9:
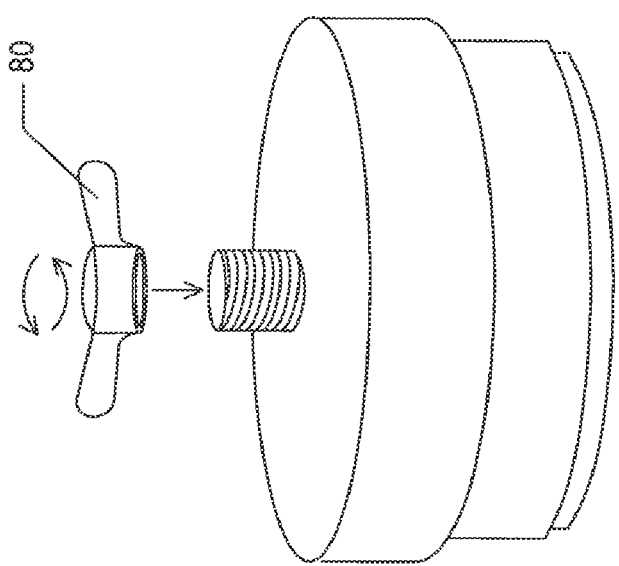
FIG. 9 is a perspective drawing showing one embodiment of the invention wherein the array of plungers is actuated via a wing nut.

Still other embodiments of the invention are possible, such as for example use of a wing nut 80 attached to screw 70 for actuating the plungers 41 (see FIG. 9). In such embodiment, the housing 50 would not comprise screw threads 71 but instead only a smooth bore past which the threaded central rod 60 can pass. In such embodiment, the operator would not need to rotate the housing but only the wing nut.

Still other embodiments of the invention are possible, such as use of inanimate means to actuate the array of plungers. For example, rather than employing animate force to work a wing nut, thumb wheel, or drive screw, the plungers can be actuated by a motor driven plunger. In such embodiment a motor can be placed in arrangement with the housing 50 to, for example, cause bidirectional rotation of the housing with respect to the embodiment disclosed in FIGS. 6-8. Likewise a motor can be affixed to gears as in the thumb wheel embodiment to actuate raising and lowering the plungers. Further, as one of ordinary skill in the art would understand, the device can include indicators to provide the operator notice when the plungers have reached their respective maximum of travel into or away from the wells 31.

Still further embodiments include use of any variety of energizing parameters including use of monopolar and/or bipolar pulses in any form, including without limitation, trains of pulses, exponential decaying pluses, square pulses, etc. Further still, the invention can use pulses having a field strength of between 10 and 1500 V/cm. Moreover, the invention contemplates the capacity to energize each electrode of the array individually or together with any combination of the remaining electrodes. For example, in one embodiment, any 4 adjacent electrodes can be pulsed such that two are positive and an opposing pair of electrodes are both negatively charged. Such pulsing provides "opposed pair" pulsing as disclosed in U.S. Pat. Nos. 5,993,434 and 5,702,359. In yet other pulsing formats, single pairs of electrodes can be energized to impart an electroporating pulse of energy to the tissue until all adjacent pairs of electrodes are energized at least once. Although not shown in the figures, it is to be understood that the invention device as disclosed in its various embodiments includes individually addressed electrode needles. This is accomplished by incorporating within substrate 22 such as by sandwich technique (i.e., substrate 22 can comprise a two layer construction with electric leads placed on a grid in between the two layers) electric lead connections running from the electrodes to the side of the device (as depicted as leads 24) terminating in plug 25 having multiple pin connector capability.

Example IV

In this example, a series of experiments were performed in mice wherein tumor recurrence rates were determined after surgery alone or after surgery and EPT. Specifically, this experiment comprises an in vivo study to establish the efficacy of EPT on surgical margin treatment in nude mice after subcutaneous introduction of HT-29 human colon carcinoma cells and resection of the tumors that arise from such introduction. The experiment was conducted under humane conditions with respect to treatment of the test animals.

The experimental design was as follows. Normal Athymic Nude female mice 4-6 weeks of age were placed in 8 groups of six mice each, except for Group 1 which comprised 10 animals and Group 3 comprising 7 animals. The HT-29 cell line is derived from a human colon carcinoma and is an aggressive fast-growing tumor in mice. In each group the animals received HT-29 human tumor cells in the form of two adjacent inocula of $5 \times 10^6$ cells using a 21 gauge needle and syringe. The HT-29 cell line was obtained from ECACC (#HTB-38), grown in McCoy's 5a medium (modified) with 1.5 mM L-glutamine adjusted to contain 2.2 g/L sodium bicarbonate, 90%, and fetal bovine serum, 10%. Cells were divided 1:2 to 1:4 on growth cycles until sufficient cells were available to use in this experiment.

Following inoculation the tumors became established at the site of the inoculations. The tumor volume on each animal was monitored regularly and calculated using the formula: Tumor volume=$(a^2 \times b/2)$ where 'a' is the smallest diameter and 'b' is the largest diameter perpendicular to 'a'. Tumors were measured three times per week starting from the day the tumors were palpable by hand. The tumors were allowed to progress until the size was between 500 and 1500 cubic millimeters. Surgical tumor removal, partial removal, or no removal was then performed in association with either EPT or no EPT. In these experiments EPT means treatment with Bleomycin and electroporation (EP). The EP, where performed, was conducted with one pulse cycle (i.e., 6 pulses at 4 Hz) per electrode insertion using a standard MedPulser generator (Genetronics, Inc. San Diego, CA) and an applicator with a disposable six needle array of 1 cm diameter, a distance between electrodes of 0.86 cm, and 1 cm needle length. Each square pulse had a duration of 100 usec and an applied voltage of 1500 V. For Groups 4-8 and 10 and 11, after intratumoral injection of Bleomycin the needle electrode array was inserted in such a way as to encompass the tumor within the needle array or, in the case of the largest tumors, such that the needles penetrated the edge of the tumor. The needle array was inserted percutaneously and essentially perpendicular to the surface of the flank of the mouse carrying the tumor. Alternatively, in those cases where the tumor was excised first, followed by i.v. injection of Bleomycin and then by EP, the needle electrode array was inserted percutaneously encompassing the surgical wound area (Groups 5-8).

Where Bleomycin was used in the experiment, it was injected at 4 U/ml saline (1U=1 mg) as uniformly as possible into tumor and margin tissues, as indicated, at a dose of 0.25 ml/cm³ volume of tissue to be treated. Alternatively, where indicated, a corresponding amount of Bleomycin was injected into the tail vein.

The experiment used 8 cohorts of at least 6 mice each. Each cohort was subjected to a treatment regimen of a combination of any of EP, Bleomycin, saline instead of Bleomycin, complete tumor excision, partial tumor excision, and no tumor excision. Tables II and III disclose the treatment regimens.

TABLE II

| Group # | Mouse # | Excision Remove entire tumor | Excision Partially remove tumor | Excision No removal of tumor | Bleomycin Intraveneous delivery | EP |
|---|---|---|---|---|---|---|
| 1 | 1-1 | X | | | X | X |
| | 1-2 | X | | | X | X |
| | 1-3 | X | | | X | X |
| | 1-4 | X | | | X | X |
| | 1-5 | X | | | X | X |
| | 1-6 | X | | | X | X |
| | 1-7 | X | | | X | X |
| | 1-8 | X | | | X | X |
| | 1-9 | X | | | X | X |
| | 1-10 | X | | | X | X |
| 2 | 2-1 | X | | | Saline | Sham |
| | 2-2 | X | | | Saline | Sham |
| | 2-3 | X | | | Saline | Sham |
| | 2-4 | X | | | Saline | Sham |
| | 2-5 | X | | | Saline | Sham |
| | 2-6 | X | | | Saline | Sham |
| 3 | 3-1 | | X | | X | X |
| | 3-2 | | X | | X | X |
| | 3-3 | | X | | X | X |
| | 3-4 | | X | | X | X |
| | 3-5 | | X | | X | X |
| | 3-6 | | X | | X | X |
| | 3-7 | | X | | X | X |
| 4 | 4-1 | | X | | Saline | Sham |
| | 4-2 | | X | | Saline | Sham |
| | 4-3 | | X | | Saline | Sham |
| | 4-4 | | X | | Saline | Sham |
| | 4-5 | | X | | Saline | Sham |
| | 4-6 | | X | | Saline | Sham |

For experiments on animals listed in Table II, the animals were anaesthetized, followed by removal or partial removal of the tumor as indicated, followed in turn by intraveneous (i.v.) injection of Bleomycin or saline. The Bleomycin dose was dependent on tumor size as described above. After 3 to 4 minutes, the animals indicated were treated with EP followed by closure of the wound with clips and surgical adhesive. In cohort 1, the entire tumor was surgically removed (see, for example FIGS. 12B and C) and the animals treated with Bleomycin and EP. In cohort 2, the tumors were removed from the animals but only saline was injected instead of Bleomycin and no EP was performed. Only a "sham" EP procedure was performed in that the electrode array was inserted into the tissue but the electrodes were not pulsed. In cohort 3, the tumors were partially (at least 95%) removed followed by Bleomycin injection and electroporation. In cohort 4, the tumors were again partially removed followed by saline injection and sham EP.

TABLE III

| Group # | Mouse # | Excision Remove entire tumor | Excision Partially remove tumor | Excision No removal of tumor | Bleomycin Intratumoral delivery | EP |
|---|---|---|---|---|---|---|
| 5 | 5-1 | X | | | X | X |
| | 5-2 | X | | | X | X |
| | 5-3 | X | | | X | X |
| | 5-4 | X | | | X | X |
| | 5-5 | X | | | X | X |
| | 5-6 | X | | | X | X |
| 6 | 6-1 | | | X | X | X |
| | 6-2 | | | X | X | X |
| | 6-3 | | | X | X | X |
| | 6-4 | | | X | X | X |
| | 6-5 | | | X | X | X |
| | 6-6 | | | X | X | X |
| 7 | 7-1 | | X | | X | X |
| | 7-2 | | X | | X | X |
| | 7-3 | | X | | X | X |
| | 7-4 | | X | | X | X |
| | 7-5 | | X | | X | X |
| | 7-6 | | X | | X | X |
| 8 | 8-1 | | | X | X | X* |
| | 8-2 | | | X | X | X* |
| | 8-3 | | | X | X | X* |
| | 8-4 | | | X | X | X* |
| | 8-5 | | | X | X | X* |
| | 8-6 | | | X | X | X* |

In Table III the cohort animals were anaesthetized followed by intratumoral administration of Bleomycin solution at a dose and volume as described above. EP was performed 10 minutes after drug administration followed by tumor removal or partial tumor removal 15 minutes later, followed in turn by wound closure. In cohort 8, EP was performed incompletely (denoted by * in Table III) in that the needle array electrodes were placed such that effective electroporation only occurred in about 75% of the tumor and associated margin tissue. In other words, the EP treatment was offset with respect to the tumor.

In addition to the above experiments, we also increased the time between completion of EPT and tumor excision to assess both gross consistency of tumor tissue and evaluate it histologically. For this purpose, three additional cohort Groups 9, 10, and 11 were used. The experimental regimen is shown in Table IV.

TABLE IV

| Group # | Mouse # | Excision Complete tumor removal | Bleomycin | EP |
|---|---|---|---|---|
| 9 | 9-1 | X | | |
| | 9-2 | X | | |
| | 9-3 | X | | |
| 10 | 10-1 | X (at 2hr) | X | X |
| | 10-2 | X (at 2hr) | X | X |
| | 10-3 | X (at 2hr) | X | X |
| 11 | 11-1 | X (at 24hr) | X | X |
| | 11-2 | X (at 24hr) | X | X |
| | 11-3 | X (at 24hr) | X | X |

The animals of Group 9 were anaesthetized followed by complete excision of the tumors. The tumors were examined for consistency and preserved in formalin for later histological evaluation, as were the tumor tissues of cohorts 10 and 11. Anaesthetized animals of cohort 10 were subjected to intratumoral administration of Bleomycin solution at a dose and volume as described above. EP was performed 10 minutes after drug administration. Tumors were excised 2 hrs after EP. Animals of cohort 11 were treated as those in cohort 10 except that their tumors were completely removed at 24 hrs after EP. All wounds were closed as described above.

Results

Figure 15:
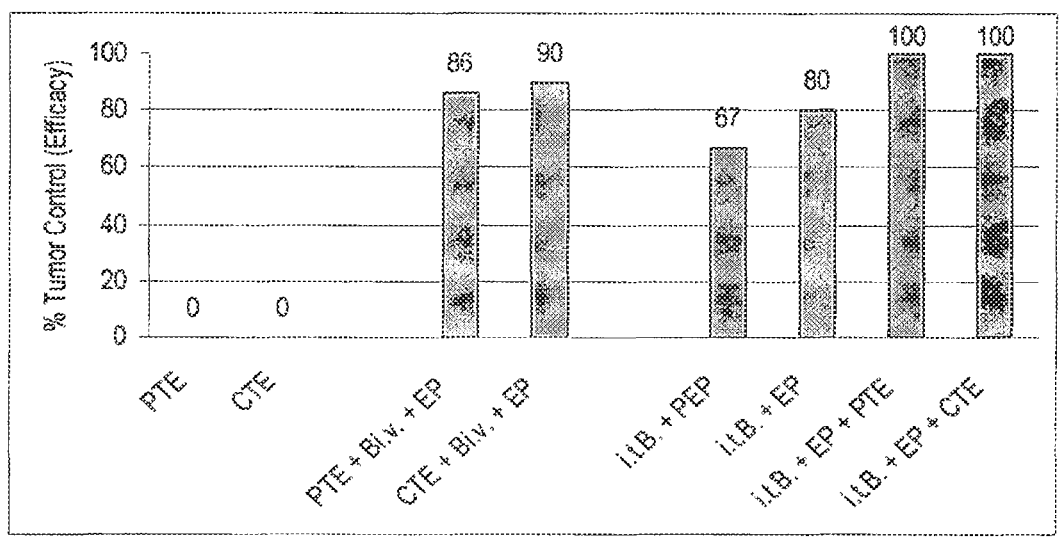
FIG. 15 shows a bar graph of the data presented in Table V. PTE refers to partial tumor excision, CTE refers to complete tumor excision, Bi.v. means Bleomycin administered to test animals intraveneously, EP means electroporation, i.t.B refers to Bleomycin administered intratumorally, and PEP means partial electroporation.

With respect to the above cohorts 1 to 8 we examined the rate of recurrence of the tumors in the test animals three weeks after treatment. As disclosed in Table V and FIG. 15, the majority of animals receiving Bleomycin and EP were protected from tumor recurrence. (see description of FIG. 15 for definitions of abbreviations therein).

TABLE V

| Group # | Tumor excision | | | EP | Route of administration of Bleomycin | | % efficacy* |
|---|---|---|---|---|---|---|---|
| | complete | partial | none | | i.v. | intratumoral | |
| 1 | + | | | + | + | | 90 |
| 5 | + | | | + | | + | 100 |
| 7 | | + | | + | | + | 100 |
| 6 | | | + | + | | + | 80 |
| 3 | | + | | + | + | | 67 |
| 8 | | + | | +/−** | | + | 67 |
| 2 | + | | | − | | | 0 |
| 4 | | + | | − | | | 0 |

*% efficacy is based on the number of test animals in each Group that did NOT experience tumor growth post treatment
**+/− represents a partial EPT procedure wherein the treatment was off-centered from the tumor/tumor bed.

Specifically, Groups 1 to 8 provide results indicating that treatment of tumor bed tissue provides an unexpected and surprising benefit in protecting the animal from recurrent tumors at the site of the treatment. As shown by the data, excision alone is not effective, whether the tumors were completely or partially removed. This is likely due to the aggressive nature of the tumor type used which left invasive tumor segments and/or micrometastases at or close to the tumor site despite careful surgical removal of the tumor correlating to similar aggressive tumors in man. This mimics situations encountered in human surgical therapy although recurrence rates in humans are generally in the 10 to 40% range and not as high as observed in this mouse experiment. Importantly, as exhibited by the results of the partial tumor removal, use of EPT with Bleomycin is associated with substantial reduction in tumor recurrence even if the surgical procedure failed (in this case on purpose) to excise all of the tumor mass. Further, the route of administration does not appear to play a significant role in efficacy in that administration by i.v. and i.t., respectively, produced similar results. Further still, the efficacy effect was surprisingly provided even after a 15 minute (interval between completion of Bleomycin-EP treatment and tumor excision. The data are further supportive of the treatment methods in effectively treating microtumor seeding in the tissue in that the experiment wherein EP was only partially performed without tumor removal, i.e. the effective electrical field was off-centered from the tumor. Here, there was still 67% efficacy indicating there was at least a microregional effect caused by the EPT. In this example study cohorts for testing Bleomycin administration alone without EP or vice versa (i.e. EP without Bleomycin) were not included as Bleomycin administration without EP is known to have no significant antitumoral activity.

Figure 11A:
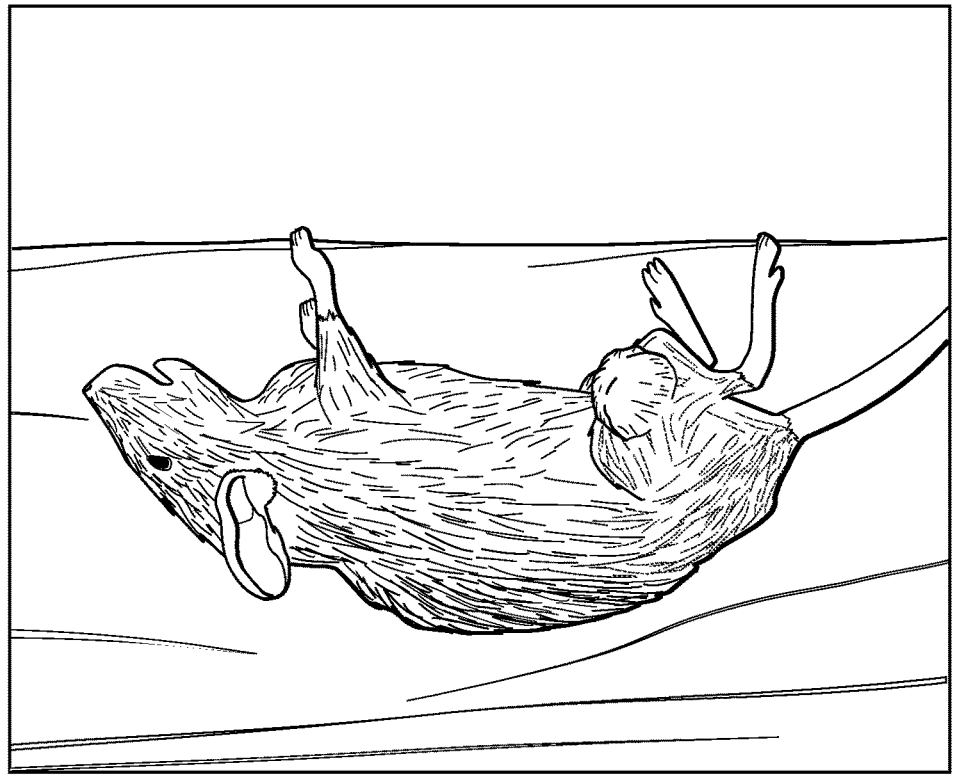
FIGS. 11A, B, C, and D are photographs of Group 2 cohort animals showing the test animal with tumor (A), the tumor surgically exposed prior to complete tumor removal (B), the open wound bed after tumor removal but prior to sham EP (C), and the surgical/treatment site after 3 weeks post treatment (D). With this Group 2, no electroporation was performed and the tumor recurred even though the tumor had been completely removed.
Figure 11B:
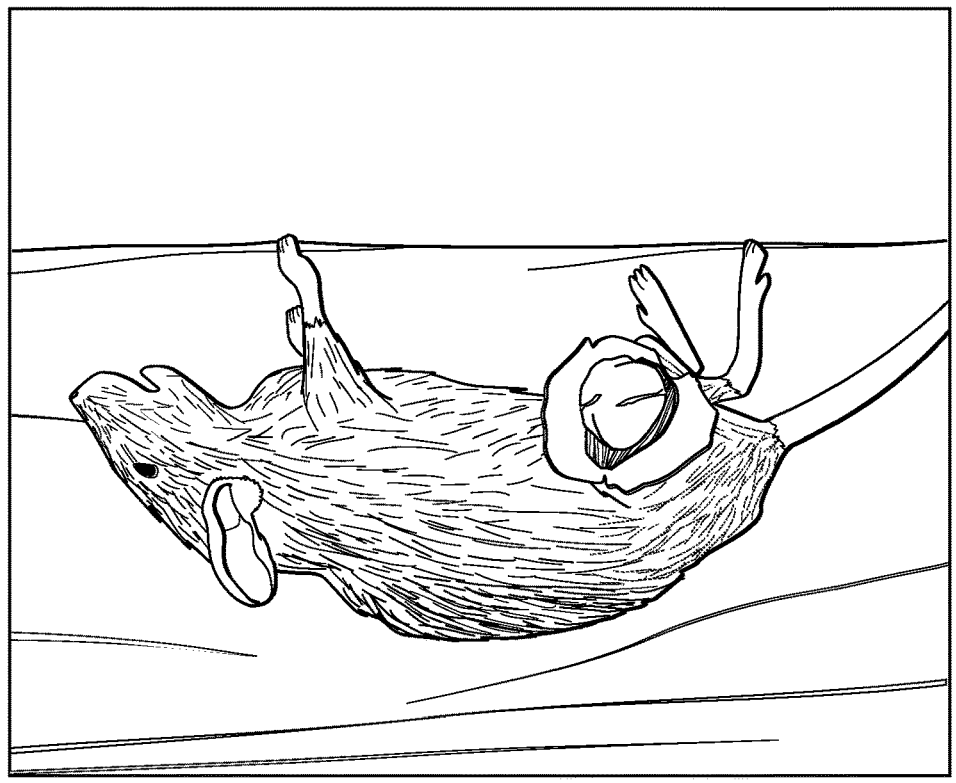
Figure 11C:
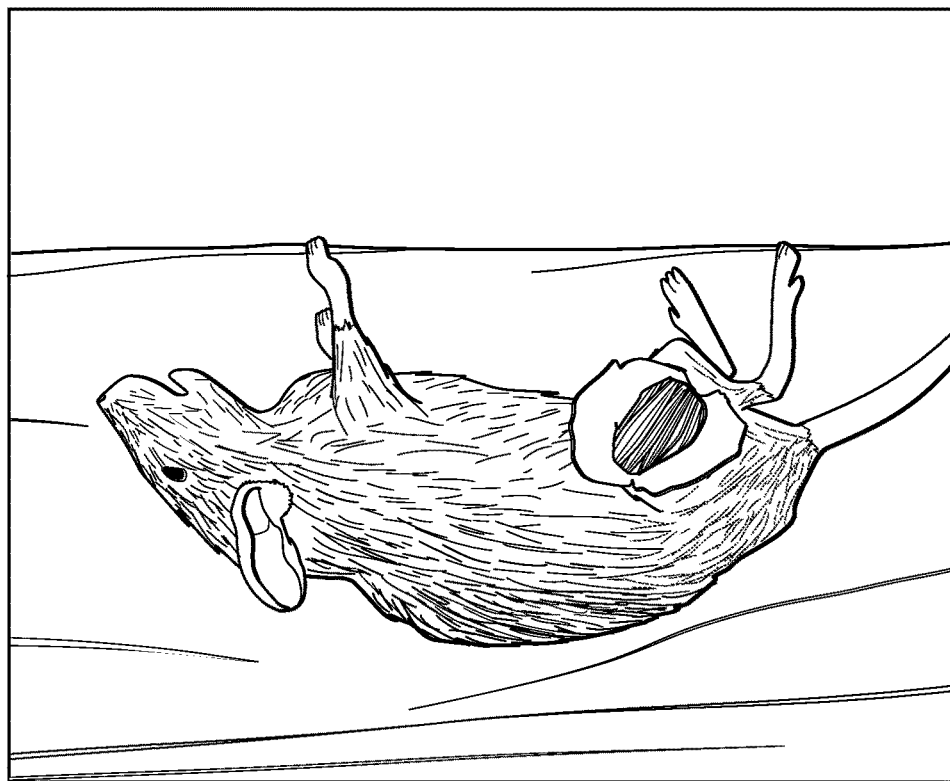
Figure 12A:
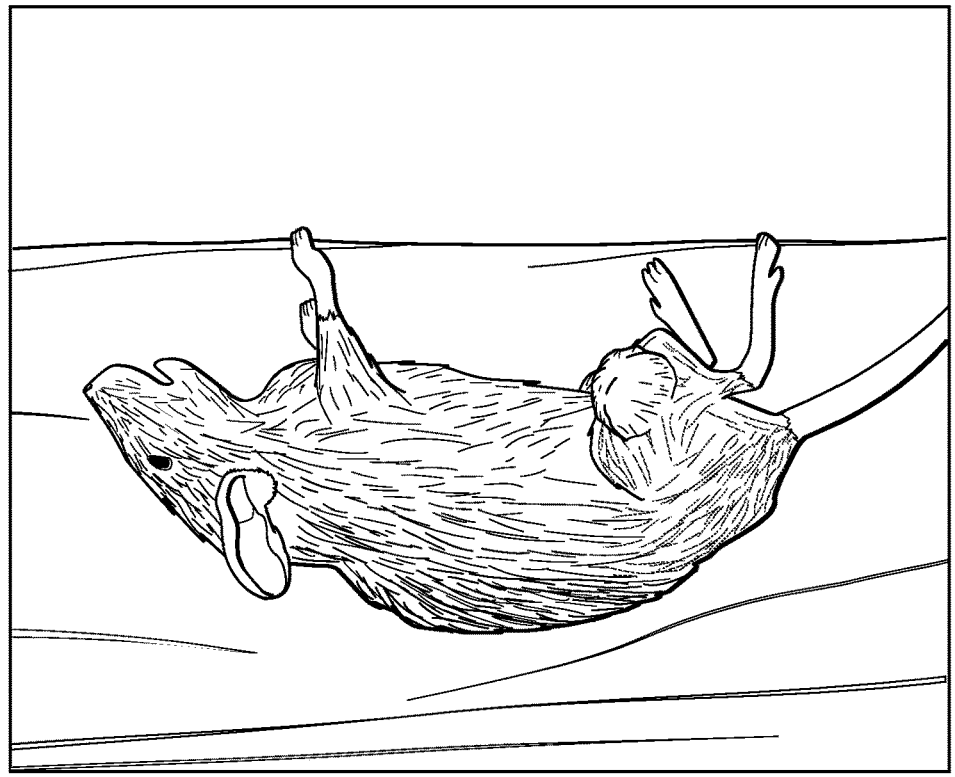
FIGS. 12A, B, C, and D are photographs of Group 1 cohort animals showing the test animal with tumor (A), the tumor surgically exposed prior to complete tumor removal (B), the open wound bed after tumor removal but prior to treatment with EP (C), and the surgical/treatment site after 3 weeks post treatment (D). As observed with Bleomycin-EP treatment no tumor recurred at the site of treatment.
Figure 12B:
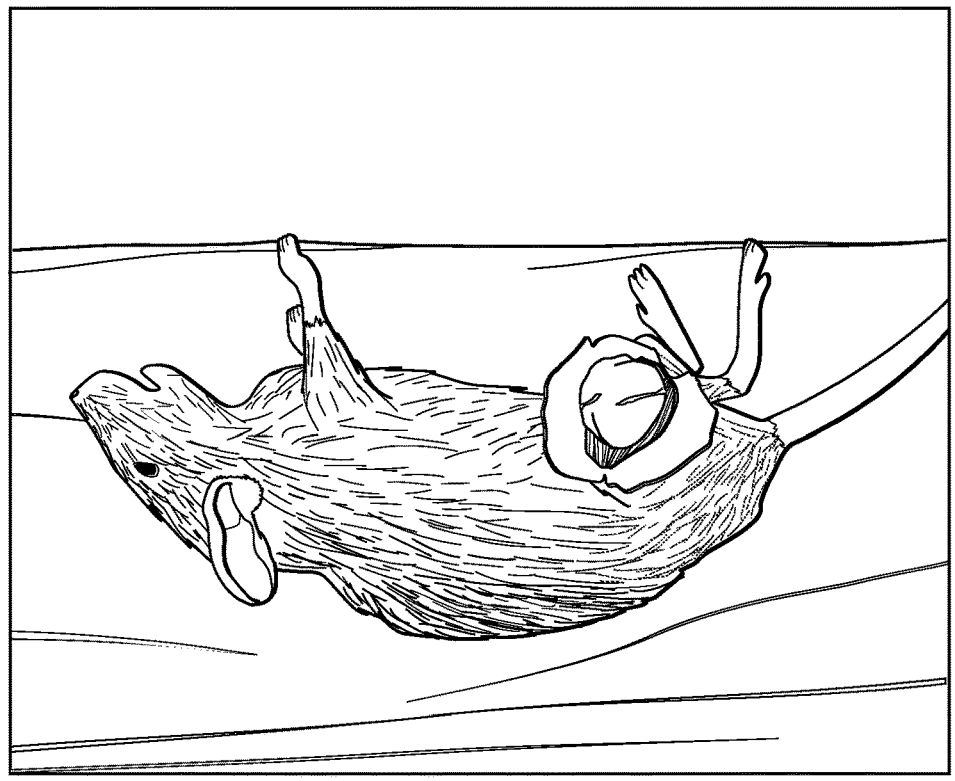
Figure 12C:
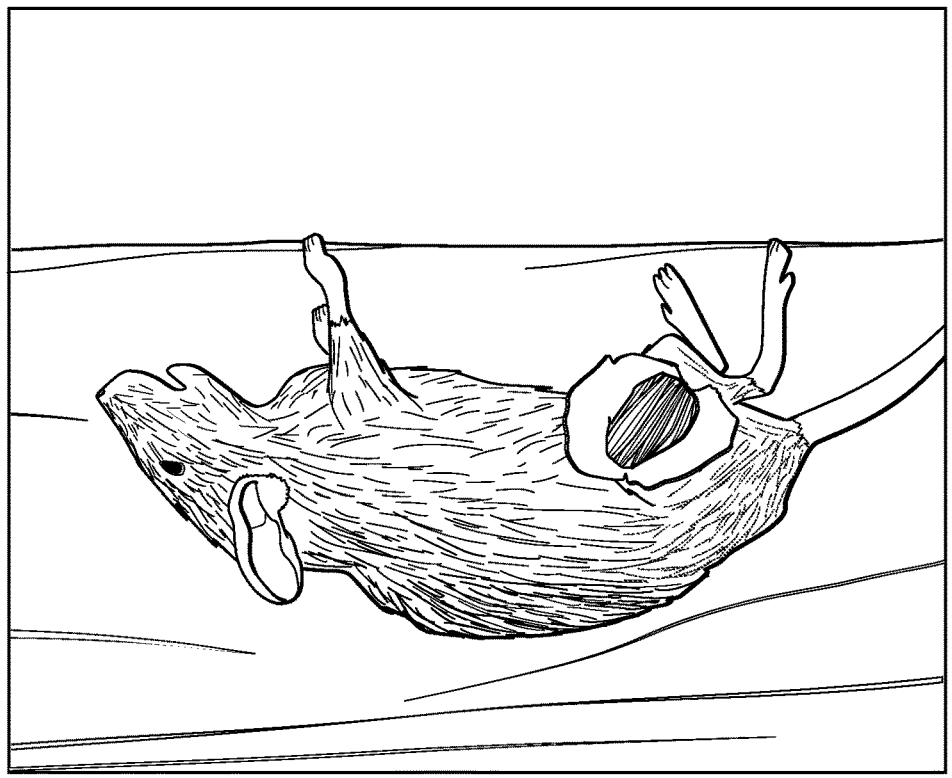
Figure 13A:
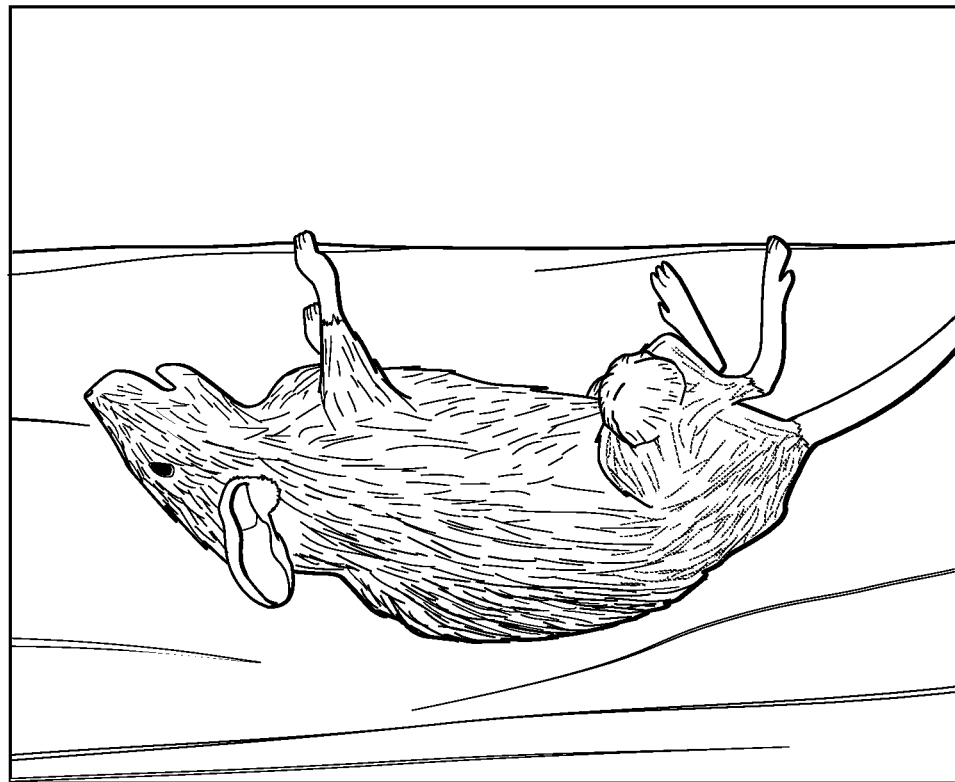
FIGS. 13A, B, and C are photographs of Group 7 cohort animals showing the test animal with tumor (A), after partial tumor removal (B), and the surgical/treatment site after 3 weeks post treatment (C). The mouse at 3 weeks showed no tumor recurrence even though the tumor was only partially removed.
Figure 13B:
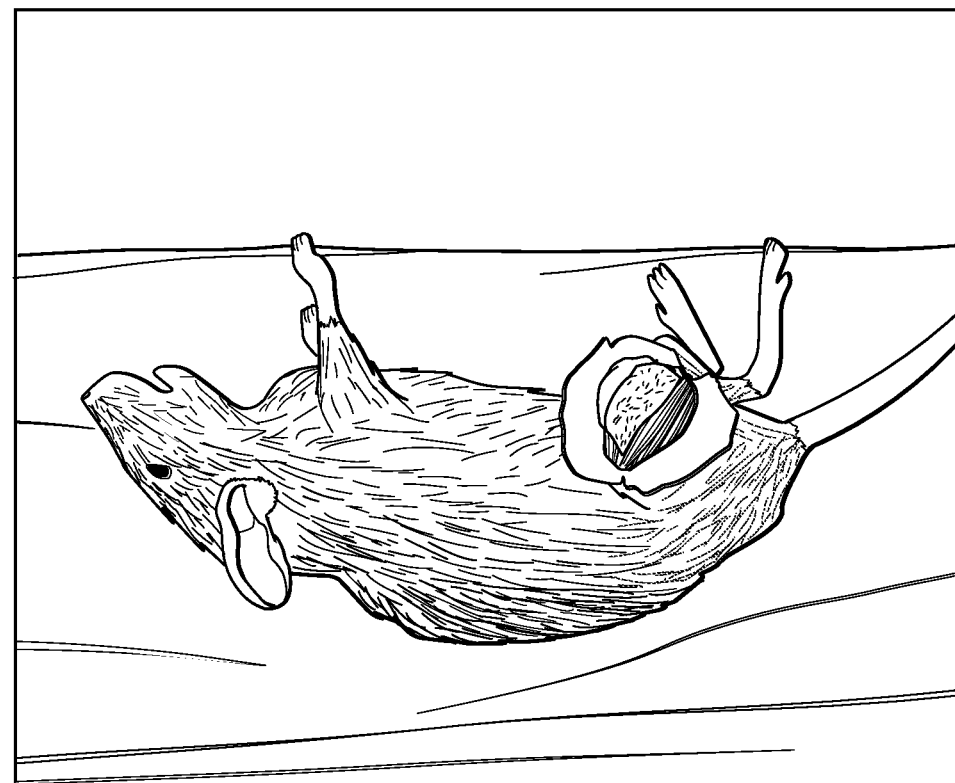

With respect to the tumor cells introduced into the test animals, we allowed the tumor masses to grow to relatively large size. See FIGS. 11A, 12A, 13A and 14A which represent tumors in test animals prior to treatment. FIGS. 11B and 12B represent examples of surgical tumor removal at the stage of having the tumor exposed before the final excision. FIGS. 11C, 12C, 13B, and 14B represent examples of the wound after complete tumor removal prior to Bleomycin-EPT (FIG. 12C) or saline-sham EP treatment (FIG. 11C), or after partial tumor removal prior to saline-sham treatment (FIG. 14B), or 15 minutes after i.t. Bleomycin-EPT (FIG. 13B).

Figure 11D:
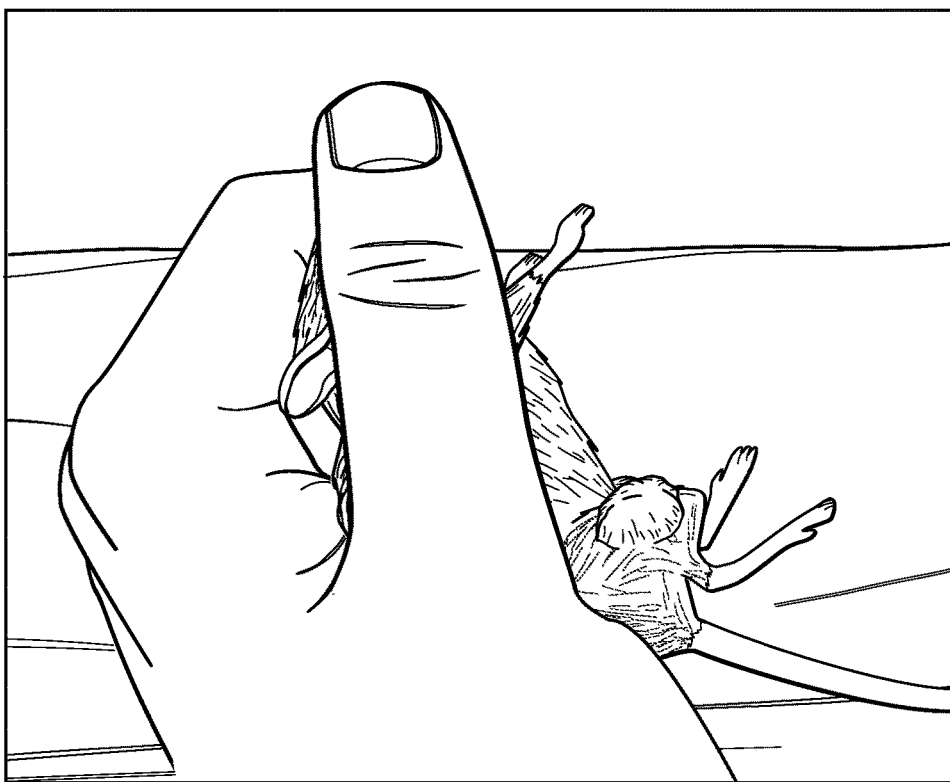
Figure 12D:
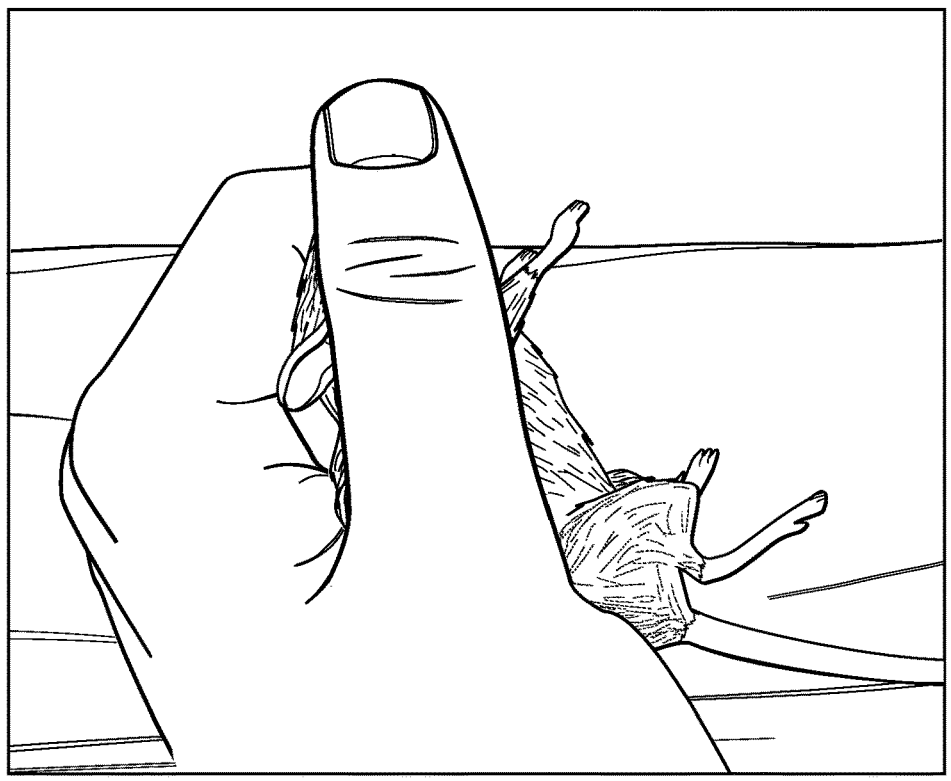
Figure 13C:
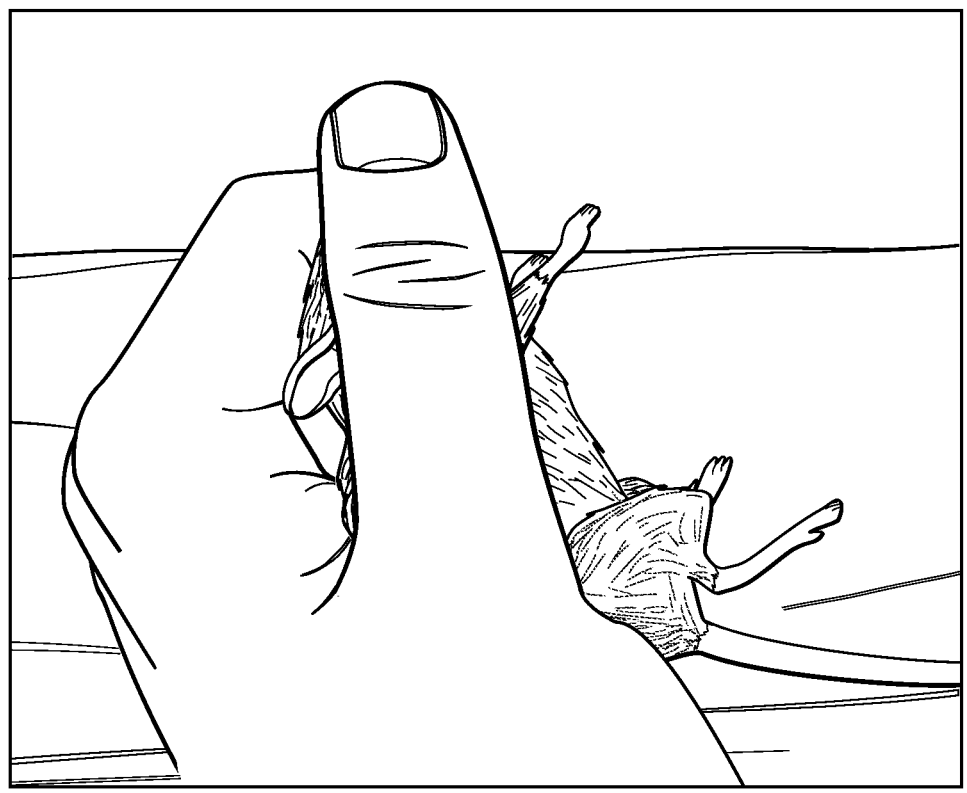
Figure 14A:
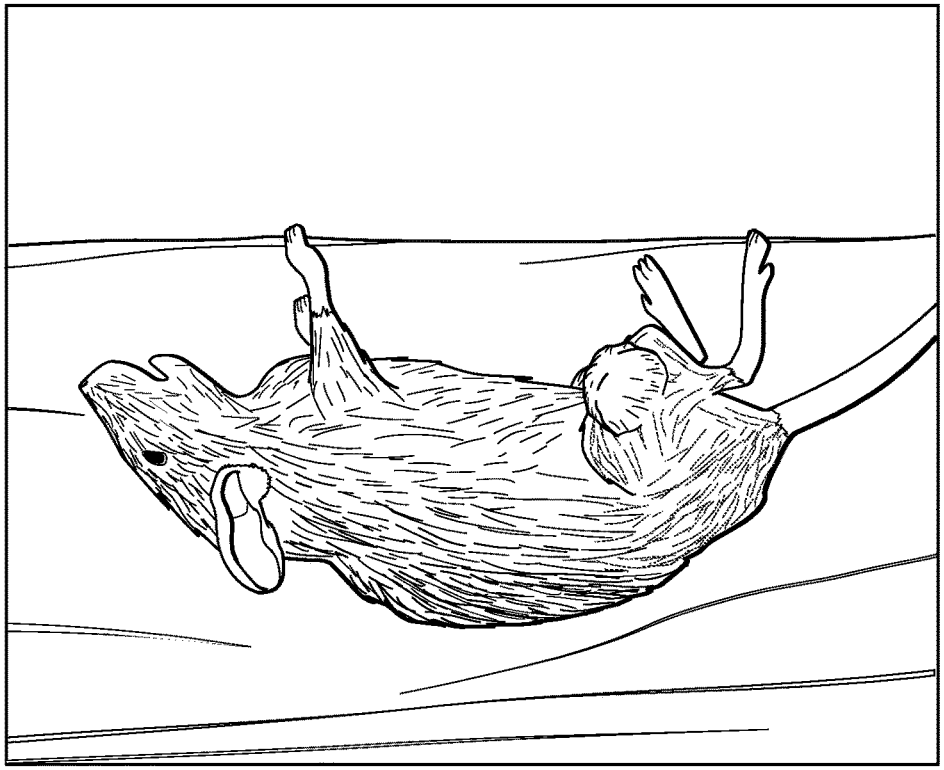
FIGS. 14A, B, and C are photographs of Group 4 cohort animals showing the test animal with tumor (A), after partial tumor removal (B), and the surgical/treatment site after 3 weeks post treatment (C). Without EPT the tumor continued to grow.
Figure 14B:
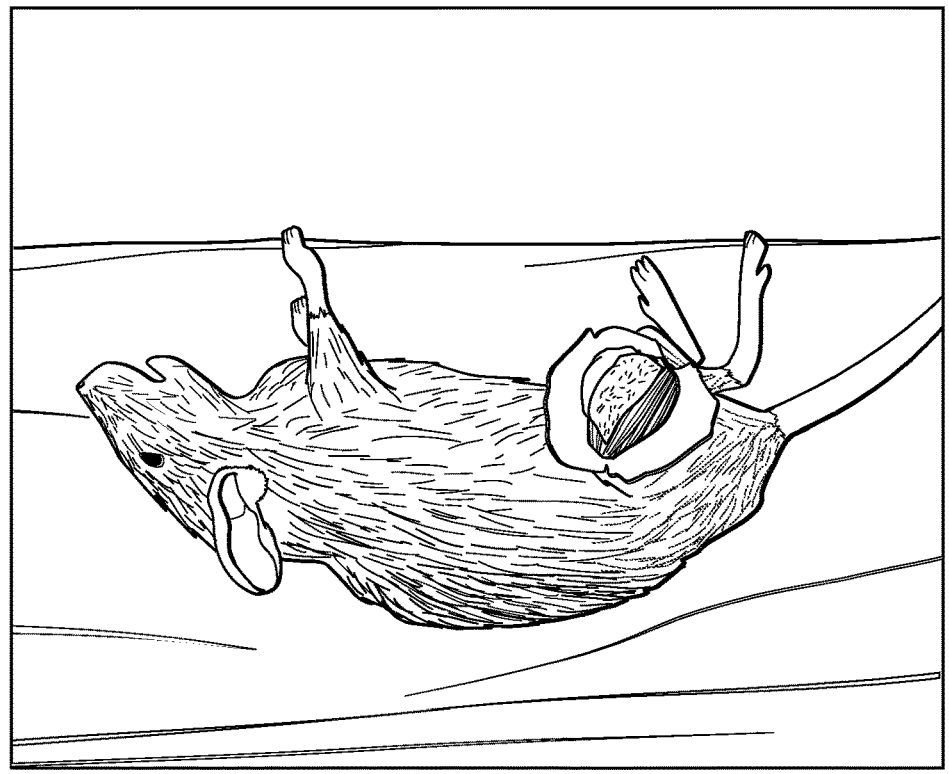
Figure 14C:
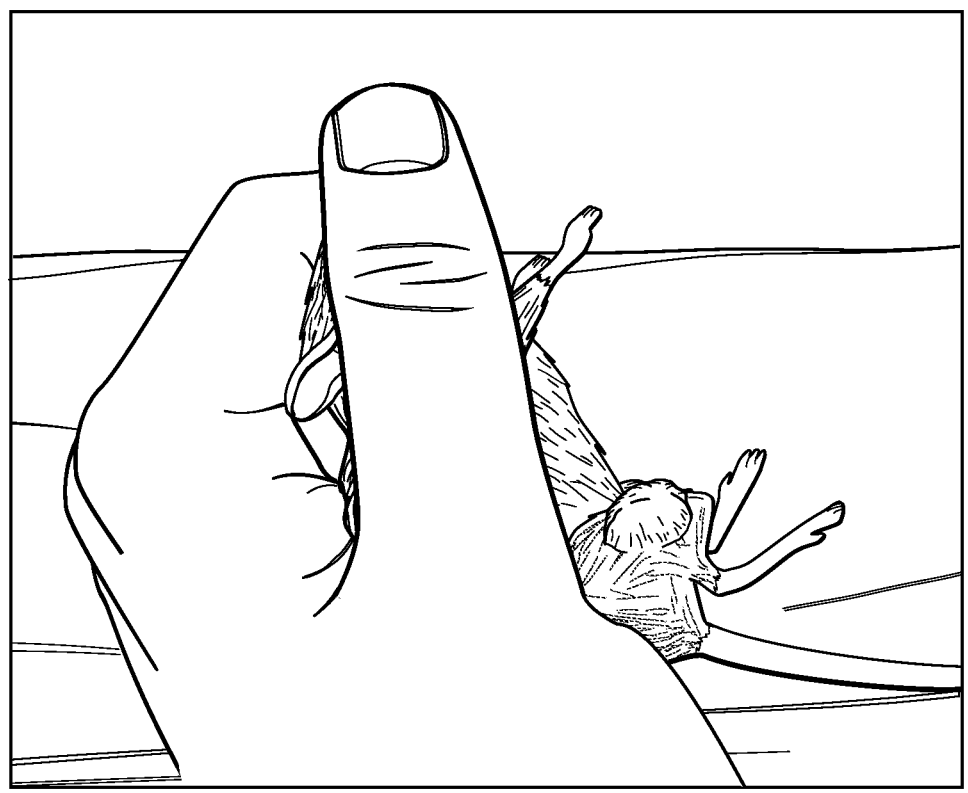

FIG. 11D shows recurring tumor after complete tumor excision and saline-sham EP treatment and FIG. 14C shows recurring tumor after partial tumor excision and saline-sham EP treatment. FIGS. 12D and 13C show tumor sites free of tumor after tumor excision and treatment with i.v. Bleomycin and EP, or treatment with i.t. Bleomycin and EP with subsequent partial tumor excision, respectively. These procedures have advantages over present standard procedures that treat cancers with anticancer drug i.t. or i.v. Excision of the tumor, either prior to or after drug-EPT treatment prevents formation of a large necrotic mass at the tumor site which the body has to resorb or otherwise eliminate, which empirically takes at least several weeks and enhances the probability of complications. Removal of the tumor prior to or after drug-EPT is likely to expedite wound healing and reduce potential complications. Further with this invention methodology, both intratumoral and intravenous injection of drug can be used.

With respect to cohorts 9-11, we observed that the consistency of the tumor changed progressively with time after treatment. When the tumor was excised two hours after treatment (cohort 10) its consistency was softer, less well defined and it leaked edemic fluid but relatively little blood. Tumors excised 24 hrs after treatment (cohort 11) had completely softened to a consistency sometimes referred to as liquefactive necrosis. At that time point surgical excision was somewhat difficult because the boundaries of the tumor were ill defined as compared to the solid tumor tissue mass of cohort 9 animals. Interestingly, we also noticed a softening of the tumor even 15 minutes after treatment when we removed tumors from cohorts 5 and 7, which made it slightly more difficult to perform surgical removal with well defined boundaries than in the case of untreated tumors. However, this did not affect the success of the treatment since both cohorts 5 and 7 showed no tumor recurrence. These observations provide proof of the opportunity of using drug, such as Bleomycin or other anticancer agent, in combination with EPT as adjuvant or tumor debulking therapy that can additionally be used alone or in conjunction with other cancer therapies. For example, a tumor could be treated with Bleomycin-EPT, the disintegrated tumor material be removed by a simple minimally invasive procedure, and if desired, followed by conventional treatments such as radiation or chemotherapy, or other tumor therapy modalities. Easy removal of the liquefied tumor material can also allow the wound to heal faster and with fewer complications, especially in the case of large tumors.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive. All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of reducing recurrence of tumor cell growth in a mammalian tissue, the method comprising:
   (a) resecting a tumor;
   (b) administering an agent capable of reducing tumor cell growth to a margin tissue after resecting the tumor; and
   (c) applying at least one electroporative electric pulse to the margin tissue after resecting the tumor, thereby delivering the agent into cells of the margin tissue;
wherein recurrence of tumor cell growth in the mammalian tissue is reduced,
   wherein the electroporative electric pulse is administered using an electroporation device comprising:
   an array of a multiplicity of electrodes capable of channeling a fluid volume from at least one variable volume reservoir to the margin tissue around the tumor when the multiplicity of electrodes are positioned in the margin tissue around the tumor,
   wherein said multiplicity of electrodes can be further energized in a predetermined format selected from the group consisting of energizing single pairs of electrodes, energizing opposed pairs of electrodes, energizing a selected portion of said electrodes sequentially, and energizing a selected portion of said electrodes simultaneously,
   wherein the electroporation device further comprises:
the array of said multiplicity of electrodes comprising lumens running therethrough for transporting a fluid medium;
   an array of compartments capable of containing a fluid medium and in fluid communication with said lumens;
   an array of plungers corresponding to said array of compartments wherein a plunger is fit into each compartment of said array of compartments and wherein said plungers are capable of slidably adjustable positioning in their respective compartments;
   an actuator for slidably adjusting positioning of said plungers, wherein the actuator is an electric motor; and
   a source of electrical energy connectable to said multiplicity of electrodes for imparting to said multiplicity of electrodes the electroporative electric pulse.

2. The method of claim 1, wherein the agent is selected from the group consisting of a chemotherapeutic drug, bleomycin, cisplatin, a polypeptide, an antibody, an RNAi, an antisense nucleic acid, an expressible gene encoding a therapeutically active polypeptide, a chemokine, and a cytokine.

3. The method of claim 1, wherein administering the agent to the margin tissue comprises intravenous administration.

4. The method of claim 1, wherein a tumor cell in the mammalian tissue is selected from the group consisting of: a cancer cell in cutaneous tissue, a cancer cell located on a head or neck of a mammal, a squamous cell carcinoma, a colon carcinoma, and a melanoma cell.

5. The method of claim 1, wherein the electroporative electric pulse comprises a pulse having a nominal field strength selected from the group consisting of: between 800 and 1500 V/cm, between 600 and 1500 V/cm, between 600 and 1400 V/cm, between 200 and 800 V/cm, between 1 and 600 V/cm, between 200 to 600 V/cm, between 400 and 600 V/cm, 1200 V/cm, and 1500 V/cm.

6. The method of claim 1, further comprising administering one or more additional cancer therapies.

7. The method of claim 6, wherein the one or more additional cancer therapies is selected from the group consisting of: radiation, chemotherapy, and antibody therapy.

8. The method of claim 1, wherein the method comprises reducing microtumor seeding in the margin tissue.

9. The method of claim 1, wherein resecting the tumor comprises partially removing the tumor.

10. The method of claim 1, wherein resecting the tumor comprises removing a primary tumor mass.

11. A method of reducing recurrence of tumor cell growth in a mammalian tissue, the method comprising:
   (a) administering an agent capable of reducing tumor cell growth to a tumor and a margin tissue;
   (b) applying at least one electroporative electric pulse to the tumor and the margin tissue, thereby delivering the agent into cells of the tumor and the margin tissue; and
   (c) resecting the tumor after applying at least one electroporative electric pulse to the tumor and the margin tissue;

wherein recurrence of tumor cell growth in the mammalian tissue is reduced, wherein the electroporative electric pulse is administered using an electroporation device comprising:
   an array of a multiplicity of electrodes capable of channeling a fluid volume from at least one variable volume reservoir to the margin tissue around the tumor when the multiplicity of electrodes are positioned in the margin tissue around the tumor,
   wherein said multiplicity of electrodes can be further energized in a predetermined format selected from the group consisting of energizing single pairs of electrodes, energizing opposed pairs of electrodes, energizing a selected portion of said electrodes sequentially, and energizing a selected portion of said electrodes simultaneously, wherein the electroporation device further comprises:
   the array of said multiplicity of electrodes comprising lumens running therethrough for transporting a fluid medium;
   an array of compartments capable of containing a fluid medium and in fluid communication with said lumens;
   an array of plungers corresponding to said array of compartments wherein a plunger is fit into each compartment of said array of compartments and wherein said plungers are capable of slidably adjustable positioning in their respective compartments;
   an actuator for slidably adjusting positioning of said plungers, wherein the actuator is an electric motor; and
   a source of electrical energy connectable to said multiplicity of electrodes for imparting to said multiplicity of electrodes the electroporative electric pulse.

12. The method of claim 11, wherein the agent is selected from the group consisting of a chemotherapeutic drug, bleomycin, cisplatin, a polypeptide, an antibody, an RNAi, an antisense nucleic acid, an expressible gene encoding a therapeutically active polypeptide, a chemokine, and a cytokine.

13. The method of claim 11, wherein administering the agent to the tumor and the margin tissue comprises injecting the agent into the tumor and the margin tissue.

14. The method of claim 11, wherein a tumor cell in the mammalian tissue is selected from the group consisting of: a cancer cell in cutaneous tissue, a cancer cell located on a head or a neck of a mammal, a squamous cell carcinoma, a colon carcinoma, and a melanoma cell.

* * * * *